United States Patent
Munkelt et al.

(10) Patent No.: US 10,751,498 B2
(45) Date of Patent: Aug. 25, 2020

(54) MEDICAL TUBES FOR RESPIRATORY SYSTEMS

(71) Applicant: FISHER & PAYKEL HEALTHCARE LIMITED, Auckland (NZ)

(72) Inventors: Katja Munkelt, Hermsdorf (DE); Christopher Gareth Sims, Auckland (NZ); Seth Mclay Frater, Auckland (NZ); Matthew Liam Buswell, Auckland (NZ); Gavin Walsh Millar, Auckland (NZ); David Leon McCauley, Auckland (NZ); Malcolm David Smith, Auckland (NZ); Brendan Thomas Vercoelen, Auckland (NZ); Thomas Jacques Fernand Maeckelberghe, Auckland (NZ); Kiel Anthony McCool, Auckland (NZ); Thomas James Edwards, Parnell (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1011 days.

(21) Appl. No.: 15/126,566

(22) PCT Filed: Mar. 17, 2015

(86) PCT No.: PCT/NZ2015/050028
§ 371 (c)(1),
(2) Date: Sep. 15, 2016

(87) PCT Pub. No.: WO2015/142192
PCT Pub. Date: Sep. 24, 2015

(65) Prior Publication Data
US 2017/0100556 A1    Apr. 13, 2017

Related U.S. Application Data

(60) Provisional application No. 61/954,230, filed on Mar. 17, 2014, provisional application No. 62/031,666, (Continued)

(51) Int. Cl.
*A61M 16/08* (2006.01)
*F16L 25/01* (2006.01)
(Continued)

(52) U.S. Cl.
CPC .... *A61M 16/0816* (2013.01); *A61M 16/0003* (2014.02); *A61M 16/0808* (2013.01);
(Continued)

(58) Field of Classification Search
CPC ..... A61M 16/0875; F16L 25/01; F16L 53/38; H01R 13/005; H01R 2201/12
See application file for complete search history.

(56) References Cited

U.S. PATENT DOCUMENTS

| 485,127 A | 10/1892 | Lynch |
| 2,073,335 A | 3/1937 | Connell |

(Continued)

FOREIGN PATENT DOCUMENTS

| AU | 1448473 | 9/1976 |
| AU | 2007317198 | 5/2008 |

(Continued)

OTHER PUBLICATIONS

US 10,426,912 B2, 10/2019, Buswell et al. (withdrawn)
(Continued)

*Primary Examiner* — Peter S Vasat
(74) *Attorney, Agent, or Firm* — Knobbe Martens Olson and Bear, LLP

(57) ABSTRACT

A medical tube comprises a tail to connect an embedded wire to an electrical component. The tail may comprise a
(Continued)

flattened portion and an exposed portion to facilitate attachment of the medical tube to an electrical component. The tail may comprise a second flattened portion. One or more wires, such as a heater wire or a sensor wire, may be embedded in the medical tube. The medical tube may comprise a connector that comprises a printed circuit board to which the one or more wires is attached. The connector may comprise features to support the printed circuit board, aid in assembly of the one or more wires to the connector, and protect electrical components against liquid ingress.

21 Claims, 29 Drawing Sheets

Related U.S. Application Data filed on Jul. 31, 2014, provisional application No. 62/047,536, filed on Sep. 8, 2014, provisional application No. 62/131,173, filed on Mar. 10, 2015.

(51) Int. Cl.

| | | |
|---|---|---|
| H01R 13/00 | (2006.01) | |
| A61M 16/16 | (2006.01) | |
| F16L 53/38 | (2018.01) | |
| A61M 39/10 | (2006.01) | |
| A61M 16/00 | (2006.01) | |
| A61M 16/10 | (2006.01) | |
| A61M 39/02 | (2006.01) | |

(52) U.S. Cl.
CPC .... *A61M 16/0875* (2013.01); *A61M 16/1095* (2014.02); *A61M 16/16* (2013.01); *A61M 39/10* (2013.01); *F16L 25/01* (2013.01); *H01R 13/005* (2013.01); *A61M 16/109* (2014.02); *A61M 16/161* (2014.02); *A61M 2016/003* (2013.01); *A61M 2016/0027* (2013.01); *A61M 2039/0267* (2013.01); *A61M 2205/3331* (2013.01); *A61M 2205/3368* (2013.01); *A61M 2205/3653* (2013.01); *A61M 2207/00* (2013.01); *F16L 53/38* (2018.01); *H01R 2201/12* (2013.01)

(56) References Cited

U.S. PATENT DOCUMENTS

| | | |
|---|---|---|
| 2,516,864 A | 8/1950 | Gilmore et al. |
| 2,788,936 A | 4/1957 | Kemnitz |
| 2,874,722 A | 2/1959 | Hamblin |
| 3,117,596 A | 1/1964 | Khan |
| 3,163,707 A | 12/1964 | Darling |
| 3,283,580 A | 11/1966 | Jacob et al. |
| 3,394,954 A | 7/1968 | Sarns |
| 3,495,628 A | 2/1970 | Boender |
| 3,582,968 A | 6/1971 | Buiting |
| 3,584,193 A | 6/1971 | Badertscher |
| 3,638,926 A | 2/1972 | Melville et al. |
| 3,695,267 A | 10/1972 | Hirtz et al. |
| 3,766,914 A | 10/1973 | Jacobs |
| 3,914,349 A | 10/1975 | Stipanuk |
| 3,926,223 A | 12/1975 | Petzetakis |
| 3,963,856 A | 6/1976 | Carlson et al. |
| 3,990,727 A | 11/1976 | Gallagher |
| 4,013,122 A | 3/1977 | Long |
| 4,013,742 A | 3/1977 | Lang |
| 4,033,808 A | 7/1977 | Petzetakis |
| 4,038,519 A | 7/1977 | Foucras |
| 4,038,980 A | 8/1977 | Fodor |
| 4,051,205 A | 9/1977 | Grant |
| 4,060,576 A | 11/1977 | Grant |
| 4,110,419 A | 8/1978 | Miller |
| 4,111,197 A | 9/1978 | Warncke et al. |
| 4,160,466 A | 7/1979 | Jousson |
| 4,172,105 A | 10/1979 | Miller et al. |
| 4,301,200 A | 11/1981 | Langenfeld |
| 4,333,451 A | 6/1982 | Paluch |
| 4,428,403 A | 1/1984 | Lee et al. |
| 4,430,994 A | 2/1984 | Clawson et al. |
| 4,487,232 A | 12/1984 | Kanao |
| 4,490,575 A | 12/1984 | Kutnyak |
| 4,500,480 A | 2/1985 | Cambio, Jr. |
| 4,529,867 A | 7/1985 | Velnosky et al. |
| 4,531,551 A | 7/1985 | Eichelberger et al. |
| 4,553,023 A | 11/1985 | Jameson et al. |
| 4,574,188 A | 3/1986 | Midgley et al. |
| 4,597,917 A | 7/1986 | Lunsford |
| 4,621,632 A | 11/1986 | Bartels et al. |
| 4,640,804 A | 2/1987 | Mizoguchi |
| 4,676,237 A | 6/1987 | Wood et al. |
| 4,684,786 A | 8/1987 | Mann et al. |
| 4,686,354 A | 8/1987 | Makin |
| 4,695,955 A | 9/1987 | Faisandier |
| 4,708,831 A | 11/1987 | Elsworth et al. |
| 4,710,887 A | 12/1987 | Ho |
| 4,722,334 A | 2/1988 | Blackmer et al. |
| 4,753,758 A | 6/1988 | Miller |
| 4,780,247 A | 10/1988 | Yasuda |
| 4,829,781 A | 5/1989 | Hitzler |
| 4,829,997 A | 5/1989 | Douwens et al. |
| 4,829,998 A | 5/1989 | Jackson |
| 4,844,512 A | 7/1989 | Gahwiler |
| 4,861,523 A | 8/1989 | Beran |
| 4,903,736 A | 2/1990 | Baston et al. |
| 4,911,157 A | 3/1990 | Miller |
| 4,911,357 A | 3/1990 | Kitamura |
| 4,921,642 A | 5/1990 | LaTorraca |
| 4,941,469 A | 7/1990 | Adahan |
| 4,967,744 A | 11/1990 | Chua |
| 5,031,612 A | 7/1991 | Clementi |
| 5,062,145 A | 10/1991 | Zwaan et al. |
| 5,092,326 A | 3/1992 | Winn et al. |
| 5,101,820 A | 4/1992 | Christopher |
| 5,127,442 A | 7/1992 | Blomqvist |
| 5,148,801 A | 9/1992 | Douwens et al. |
| 5,164,652 A | 11/1992 | Johnson et al. |
| 5,213,376 A | 5/1993 | Szabo |
| 5,224,923 A | 7/1993 | Moffett et al. |
| 5,230,331 A | 7/1993 | Rusz et al. |
| 5,231,979 A | 8/1993 | Rose et al. |
| 5,336,156 A | 8/1994 | Miller et al. |
| 5,346,128 A | 9/1994 | Wacker |
| 5,347,211 A | 9/1994 | Jakubowski |
| 5,367,604 A | 11/1994 | Murray |
| 5,388,443 A | 2/1995 | Manaka |
| 5,392,770 A | 2/1995 | Clawson et al. |
| 5,404,729 A | 4/1995 | Matsuoka et al. |
| 5,405,269 A | 4/1995 | Stupecky |
| 5,428,752 A | 6/1995 | Goren et al. |
| 5,449,234 A | 9/1995 | Gipp et al. |
| 5,454,061 A | 9/1995 | Carlson |
| 5,482,031 A | 1/1996 | Lambert |
| 5,516,466 A | 5/1996 | Schlesch et al. |
| 5,529,060 A | 6/1996 | Salmon et al. |
| 5,537,996 A | 7/1996 | McPhee |
| 5,551,731 A | 9/1996 | Gray et al. |
| 5,558,084 A | 9/1996 | Daniell et al. |
| 5,564,415 A | 10/1996 | Dobson et al. |
| 5,588,423 A | 12/1996 | Smith |
| 5,591,292 A | 1/1997 | Blomqvist |
| 5,600,752 A | 2/1997 | Lopatinsky |
| 5,630,806 A | 5/1997 | Inagaki |
| 5,637,168 A | 6/1997 | Carlson |
| 5,640,951 A | 6/1997 | Huddart et al. |
| 5,673,687 A | 10/1997 | Dobson et al. |
| 5,759,149 A | 6/1998 | Goldberg et al. |
| 5,769,071 A | 6/1998 | Turnbull |
| 5,778,872 A | 7/1998 | Fukunaga et al. |
| 5,848,223 A | 12/1998 | Carlson |
| 5,906,201 A | 5/1999 | Nilson |
| 5,943,473 A | 8/1999 | Levine |

(56) References Cited

U.S. PATENT DOCUMENTS

| | | | |
|---|---|---|---|
| 5,988,164 A | 11/1999 | Paluch | |
| 5,991,507 A | 11/1999 | Bencsits | |
| 6,010,118 A | 1/2000 | Milewicz | |
| 6,024,694 A | 2/2000 | Goldberg et al. | |
| 6,038,457 A | 3/2000 | Barkat | |
| 6,050,260 A | 4/2000 | Daniell et al. | |
| 6,078,730 A | 6/2000 | Huddart et al. | |
| 6,095,505 A | 8/2000 | Miller | |
| 6,105,649 A | 8/2000 | Levingston et al. | |
| 6,109,782 A | 8/2000 | Fukura et al. | |
| 6,125,847 A | 10/2000 | Lin | |
| 6,138,674 A | 10/2000 | Gull et al. | |
| 6,142,974 A | 11/2000 | Kistner et al. | |
| 6,158,431 A | 12/2000 | Poole | |
| 6,167,883 B1 | 1/2001 | Beran et al. | |
| 6,189,870 B1 | 2/2001 | Withall | |
| 6,190,480 B1 | 2/2001 | Carlson | |
| 6,219,490 B1 | 4/2001 | Gibertoni et al. | |
| 6,272,933 B1 | 8/2001 | Gradon et al. | |
| 6,311,958 B1 | 11/2001 | Stanek | |
| 6,347,646 B2 | 2/2002 | Fukui et al. | |
| 6,349,722 B1 | 2/2002 | Gradon et al. | |
| 6,367,472 B1 | 4/2002 | Koch | |
| 6,367,510 B1 | 4/2002 | Carlson | |
| 6,374,864 B1 | 4/2002 | Philip | |
| 6,384,755 B1 | 5/2002 | Hayden | |
| 6,394,084 B1 | 5/2002 | Nitta | |
| 6,394,145 B1 * | 5/2002 | Bailly | F16L 11/24 138/122 |
| 6,397,841 B1 | 6/2002 | Kenyon et al. | |
| 6,397,846 B1 | 6/2002 | Skog et al. | |
| 6,398,197 B1 | 6/2002 | Dickinson et al. | |
| 6,463,925 B2 | 10/2002 | Nuckols et al. | |
| 6,474,335 B1 | 11/2002 | Lammers | |
| 6,537,405 B1 | 3/2003 | Henderson et al. | |
| 6,540,734 B1 | 4/2003 | Chiu et al. | |
| 6,543,412 B2 | 4/2003 | Amou et al. | |
| 6,564,011 B1 | 5/2003 | Janoff et al. | |
| 6,584,972 B2 | 7/2003 | McPhee | |
| 6,594,366 B1 | 7/2003 | Adams | |
| 6,668,828 B2 | 12/2003 | Figley et al. | |
| 6,691,707 B1 | 2/2004 | Gunaratnam et al. | |
| 6,694,974 B1 | 2/2004 | George-Gradon et al. | |
| 6,718,974 B1 | 4/2004 | Moberg | |
| 6,827,109 B2 | 12/2004 | Mccaughtry | |
| 6,918,389 B2 | 7/2005 | Seakins et al. | |
| 6,932,119 B2 | 8/2005 | Carlson | |
| 6,953,354 B2 | 10/2005 | Edirisuriya et al. | |
| 7,086,422 B2 | 8/2006 | Kressierer/Huber et al. | |
| 7,096,864 B1 | 8/2006 | Mayer et al. | |
| 7,120,354 B2 | 10/2006 | Mackie et al. | |
| 7,156,127 B2 | 1/2007 | Moulton et al. | |
| 7,157,035 B2 | 1/2007 | Edirisuriya et al. | |
| 7,291,240 B2 | 11/2007 | Smith et al. | |
| 7,468,116 B2 | 12/2008 | Smith et al. | |
| 7,588,029 B2 | 9/2009 | Smith et al. | |
| 7,588,186 B2 | 9/2009 | Steffen et al. | |
| 7,637,288 B2 | 12/2009 | Huber et al. | |
| 7,647,926 B2 | 1/2010 | Gerder et al. | |
| 7,766,050 B2 | 8/2010 | Patel | |
| 7,814,907 B2 | 10/2010 | Bremner et al. | |
| 7,965,930 B2 | 6/2011 | Carlson et al. | |
| 7,997,267 B2 | 8/2011 | Ging et al. | |
| 8,091,547 B2 | 1/2012 | Thudor et al. | |
| 8,122,882 B2 | 2/2012 | Mcghin et al. | |
| 8,186,345 B2 | 5/2012 | Payton et al. | |
| 8,235,041 B2 | 8/2012 | Seakins et al. | |
| 8,333,194 B2 | 12/2012 | Lewis et al. | |
| 8,333,199 B2 | 12/2012 | Landis et al. | |
| 8,360,059 B2 | 1/2013 | Koulechov et al. | |
| 8,453,641 B2 | 6/2013 | Payton et al. | |
| 8,459,259 B2 | 6/2013 | Klasek et al. | |
| 8,469,025 B2 | 6/2013 | Mayer et al. | |
| 8,522,782 B2 | 9/2013 | Lewis et al. | |
| 8,563,863 B2 | 10/2013 | Carlson | |
| 8,563,864 B2 | 10/2013 | Carlson | |
| 8,631,789 B2 | 1/2014 | Virr et al. | |
| 8,709,187 B2 | 4/2014 | Smith et al. | |
| 8,733,349 B2 | 5/2014 | Bath et al. | |
| 8,844,522 B2 | 9/2014 | Huby et al. | |
| 9,119,933 B2 | 9/2015 | Bedford et al. | |
| 9,440,040 B2 | 9/2016 | Klasek et al. | |
| 9,517,321 B2 | 12/2016 | Buechi et al. | |
| 9,555,210 B2 | 1/2017 | Seakins et al. | |
| 9,572,949 B2 | 2/2017 | Vos et al. | |
| 9,855,398 B2 | 1/2018 | Klasek et al. | |
| 10,080,866 B2 | 9/2018 | Stoks et al. | |
| 2001/0017134 A1 | 8/2001 | Bahr | |
| 2001/0050080 A1 | 12/2001 | Seakins et al. | |
| 2002/0038392 A1 | 3/2002 | De La Huerga | |
| 2002/0120236 A1 | 8/2002 | Diaz et al. | |
| 2002/0124847 A1 | 9/2002 | Smith et al. | |
| 2002/0173717 A1 | 11/2002 | Rohling et al. | |
| 2002/0186966 A1 | 12/2002 | Zimmer et al. | |
| 2003/0059213 A1 | 3/2003 | Mackie et al. | |
| 2003/0183294 A1 | 10/2003 | Carlson | |
| 2003/0236015 A1 | 12/2003 | Edirisuriya et al. | |
| 2004/0074493 A1 | 4/2004 | Seakins et al. | |
| 2004/0074495 A1 | 4/2004 | Wickham et al. | |
| 2004/0079371 A1 | 4/2004 | Gray | |
| 2004/0081784 A1 | 4/2004 | Smith et al. | |
| 2004/0099268 A1 | 5/2004 | Smith et al. | |
| 2004/0101026 A1 | 5/2004 | Nitta et al. | |
| 2004/0149284 A1 | 8/2004 | Smith et al. | |
| 2004/0182392 A1 | 9/2004 | Gerder et al. | |
| 2004/0244858 A1 | 12/2004 | Jeong | |
| 2005/0059957 A1 | 6/2005 | Byerly et al. | |
| 2005/0152733 A1 * | 7/2005 | Patel | A61M 16/08 400/625 |
| 2006/0165829 A1 * | 7/2006 | Smith | A61M 16/08 425/113 |
| 2006/0283447 A1 | 12/2006 | Dhuper et al. | |
| 2007/0047733 A1 | 3/2007 | Bremer et al. | |
| 2007/0051368 A1 | 3/2007 | Seakins et al. | |
| 2007/0079982 A1 | 4/2007 | Laurent et al. | |
| 2007/0107737 A1 | 5/2007 | Landis et al. | |
| 2007/0277828 A1 | 12/2007 | Ho et al. | |
| 2008/0078259 A1 | 4/2008 | Duff | |
| 2008/0105257 A1 * | 5/2008 | Klasek | A61M 16/0633 128/203.27 |
| 2008/0173305 A1 | 7/2008 | Frater | |
| 2008/0202512 A1 | 8/2008 | Kressierer/Huber et al. | |
| 2008/0251073 A1 | 10/2008 | Jassell et al. | |
| 2008/0264413 A1 | 10/2008 | Doherty et al. | |
| 2009/0078259 A1 | 3/2009 | Kooij et al. | |
| 2009/0078440 A1 | 3/2009 | Carlson et al. | |
| 2009/0110379 A1 | 4/2009 | McGhin et al. | |
| 2009/0126817 A1 | 5/2009 | Gray | |
| 2009/0149696 A1 | 6/2009 | Chilton, III | |
| 2009/0320840 A1 | 12/2009 | Klasek et al. | |
| 2010/0083965 A1 | 4/2010 | Virr et al. | |
| 2010/0116272 A1 | 5/2010 | Row et al. | |
| 2010/0224276 A1 | 9/2010 | Forrester et al. | |
| 2011/0023874 A1 | 2/2011 | Bath et al. | |
| 2011/0046494 A1 | 2/2011 | Balji et al. | |
| 2011/0155132 A1 | 6/2011 | Virr et al. | |
| 2011/0168287 A1 | 7/2011 | Carlson | |
| 2012/0125333 A1 | 5/2012 | Bedford | |
| 2012/0255758 A1 | 10/2012 | Lee | |
| 2013/0104888 A1 | 5/2013 | Landis et al. | |
| 2013/0104901 A1 | 5/2013 | Landis et al. | |
| 2013/0174839 A1 | 7/2013 | Ging et al. | |
| 2013/0239966 A1 | 9/2013 | Klasek et al. | |
| 2013/0255677 A1 | 10/2013 | Varga | |
| 2013/0280055 A1 | 10/2013 | Daly et al. | |
| 2013/0340752 A1 | 12/2013 | Landis et al. | |
| 2014/0037276 A1 | 2/2014 | Carlson | |
| 2014/0130802 A1 | 5/2014 | Virr et al. | |
| 2014/0202460 A1 | 7/2014 | Bath et al. | |
| 2014/0216459 A1 | 8/2014 | Vos et al. | |
| 2014/0246021 A1 | 9/2014 | Buechi et al. | |
| 2014/0311487 A1 | 10/2014 | Buechi et al. | |
| 2014/0318536 A1 | 10/2014 | Landis et al. | |
| 2014/0366876 A1 | 12/2014 | Huby et al. | |

(56) References Cited

U.S. PATENT DOCUMENTS

| | | | |
|---|---|---|---|
| 2015/0090260 A1 | 4/2015 | Seakins et al. |
| 2015/0306333 A1 | 10/2015 | Amadio et al. |
| 2016/0256657 A1 | 9/2016 | Klasek et al. |
| 2016/0271356 A1 | 9/2016 | Robertson et al. |
| 2016/0354573 A1 | 12/2016 | Buswell et al. |
| 2017/0100556 A1 | 4/2017 | Munkelt et al. |
| 2018/0280651 A1 | 10/2018 | Liu et al. |
| 2019/0076620 A1 | 3/2019 | Stoks et al. |

FOREIGN PATENT DOCUMENTS

| | | |
|---|---|---|
| CN | 2243015 Y | 12/1996 |
| CN | 1549910 | 11/2004 |
| CN | 201672170 U | 12/2010 |
| DE | 36 29 353 | 1/1988 |
| DE | 4020522 A1 | 1/1992 |
| DE | 40 34 611 | 5/1992 |
| DE | 4102223 A1 | 7/1992 |
| DE | 9200567 U1 | 7/1992 |
| DE | 33 11 811 | 10/1994 |
| DE | 94 09 231.1 | 12/1994 |
| DE | 19647548 | 5/1998 |
| DE | 19958296 | 9/2001 |
| DE | 20202906 U1 | 5/2002 |
| DE | 10312881 | 5/2004 |
| DE | 20 2004 006 484 | 9/2005 |
| DE | 202005008156 | 11/2006 |
| DE | 202006007397 U1 | 9/2007 |
| DE | 102006056781 A1 | 6/2008 |
| DE | 102007003454 | 7/2008 |
| DE | 102007003455 | 8/2008 |
| DE | 202007018764 U1 | 6/2009 |
| DE | 102011055439 A1 | 5/2013 |
| EP | 0111248 A2 | 6/1984 |
| EP | 0201985 | 2/1986 |
| EP | 0201985 | 11/1986 |
| EP | 0232864 A2 | 8/1987 |
| EP | 0 258 928 | 9/1988 |
| EP | 0342802 | 11/1989 |
| EP | 0 481 459 | 4/1992 |
| EP | 0 556 561 | 8/1993 |
| EP | 616 166 | 9/1994 |
| EP | 0621050 A2 | 10/1994 |
| EP | 0672430 A2 | 9/1995 |
| EP | 0 885 623 | 12/1998 |
| EP | 0956068 | 11/1999 |
| EP | 1078645 | 2/2001 |
| EP | 1127583 | 8/2001 |
| EP | 1 138 341 | 10/2001 |
| EP | 1145678 | 10/2001 |
| EP | 1147004 B1 | 2/2003 |
| EP | 1380276 A1 | 1/2004 |
| EP | 1396277 A2 | 3/2004 |
| EP | 1535722 A2 | 6/2005 |
| EP | 1579984 A2 | 9/2005 |
| EP | 2075026 A1 | 7/2009 |
| EP | 2079505 | 7/2009 |
| EP | 2269680 A1 | 1/2011 |
| EP | 2133611 B1 | 9/2011 |
| EP | 2269680 | 9/2012 |
| EP | 2514478 | 7/2013 |
| EP | 2689174 | 1/2014 |
| EP | 2337604 | 3/2014 |
| GB | 1 167 551 | 10/1969 |
| GB | 2056611 | 3/1981 |
| GB | 2173274 | 2/1989 |
| GB | 2 277 689 | 11/1994 |
| JP | S56-109189 U | 8/1981 |
| JP | S59-113392 | 6/1984 |
| JP | 05-317428 | 12/1993 |
| JP | 08-061731 | 3/1996 |
| JP | H08-109984 A | 4/1996 |
| JP | H09-234247 | 9/1997 |
| JP | H09-276408 | 10/1997 |
| JP | 11-033119 A | 2/1999 |
| JP | H11-286058 A | 10/1999 |
| JP | 2001-129091 | 5/2001 |
| JP | 2001-511507 A | 8/2001 |
| JP | 2003-139276 A | 5/2003 |
| JP | 2004-148817 | 5/2004 |
| JP | 4422293 B2 | 2/2010 |
| NZ | 579384 | 5/2011 |
| NZ | 587113 | 12/2011 |
| NZ | 589766 | 5/2012 |
| NZ | 575837 | 7/2012 |
| NZ | 583968 | 10/2012 |
| NZ | 597827 | 6/2013 |
| NZ | 590924 | 8/2013 |
| NZ | 600986 | 8/2013 |
| NZ | 597179 | 9/2013 |
| NZ | 605324 | 6/2014 |
| NZ | 605326 | 7/2014 |
| NZ | 607629 | 7/2014 |
| NZ | 610299 | 11/2014 |
| NZ | 701541 | 5/2015 |
| NZ | 625795 | 6/2015 |
| NZ | 620739 | 8/2015 |
| NZ | 625605 | 4/2016 |
| NZ | 710351 | 1/2017 |
| NZ | 631008 | 7/2017 |
| SU | 379270 | 4/1973 |
| WO | WO 92/21163 A1 | 11/1992 |
| WO | WO 1996/020748 A1 | 7/1996 |
| WO | WO 97/18001 A1 | 5/1997 |
| WO | WO 98/26826 | 6/1998 |
| WO | WO 01/10489 | 2/2001 |
| WO | WO 02/32486 | 4/2002 |
| WO | WO 2003/022342 | 3/2003 |
| WO | WO 2003/026721 A2 | 4/2003 |
| WO | WO 2004/024429 A1 | 3/2004 |
| WO | WO 2004/039444 A1 | 5/2004 |
| WO | WO 2004/105847 | 12/2004 |
| WO | WO 2004/105848 A1 | 12/2004 |
| WO | WO 2005/021076 | 3/2005 |
| WO | WO 2006/092001 A1 | 9/2006 |
| WO | WO 2006/095151 | 9/2006 |
| WO | WO 2007/051230 A1 | 5/2007 |
| WO | WO 2008/055308 A1 | 5/2008 |
| WO | WO 2008/060046 A1 | 5/2008 |
| WO | WO 2008/060295 | 5/2008 |
| WO | WO 2008/076230 | 6/2008 |
| WO | WO 2009/015410 A1 | 2/2009 |
| WO | WO 2009/022004 A2 | 2/2009 |
| WO | WO 2010/084183 A2 | 7/2010 |
| WO | WO 2011/051837 A1 | 5/2011 |
| WO | WO 2011/051870 | 5/2011 |
| WO | WO 2011/136665 A1 | 11/2011 |
| WO | WO 2011/162622 A1 | 12/2011 |
| WO | WO 2012/053910 A1 | 4/2012 |
| WO | WO 2012/164407 A1 | 12/2012 |
| WO | WO 2013/045575 | 4/2013 |
| WO | WO 2013/127474 | 9/2013 |
| WO | WO 2013/137753 | 9/2013 |
| WO | WO 2013/147623 A1 | 10/2013 |
| WO | WO 2013/165263 A1 | 11/2013 |
| WO | WO 2014/025266 | 2/2014 |
| WO | WO 2014/077706 | 5/2014 |
| WO | WO 2014/205513 | 12/2014 |
| WO | WO 2015/038013 A1 | 3/2015 |
| WO | WO 2015/142192 | 9/2015 |
| WO | WO 2017/043981 A1 | 3/2017 |
| WO | WO 2018/116187 | 6/2018 |

OTHER PUBLICATIONS

International Preliminary Report on Patentability; Application No. PCT/IB2012/001786; Filed May 30, 2012, dated Dec. 19, 2013, in 6 pages.
International Search Report; PCT/IB2012/001786; dated Nov. 21, 2012, in 6 pages.
International Preliminary Report on Patentability dated Jun. 9, 2015 for PCT Application No. PCT/NZ2013/000222 filed on Dec. 4, 2013.

(56) References Cited

OTHER PUBLICATIONS

MR810 Respiratory Humidifier Technical Manual, Revision C.
Fisher & Paykel Healthcare, Annual Report 2003.
Fisher & Paykel Healthcare, FY04 Full Year Overview & Update, May 24, 2004.
Fisher & Paykel Healthcare, Full Year Analyst Briefing, Jun. 5, 2002.
MR850 Respiratory Humidifier Instruction Sheet, Rev. G, Feb. 2004.
May 21, 2015 Written Opinion and International Search Report for PCT Application No. PCT/NZ2015/050028.

* cited by examiner

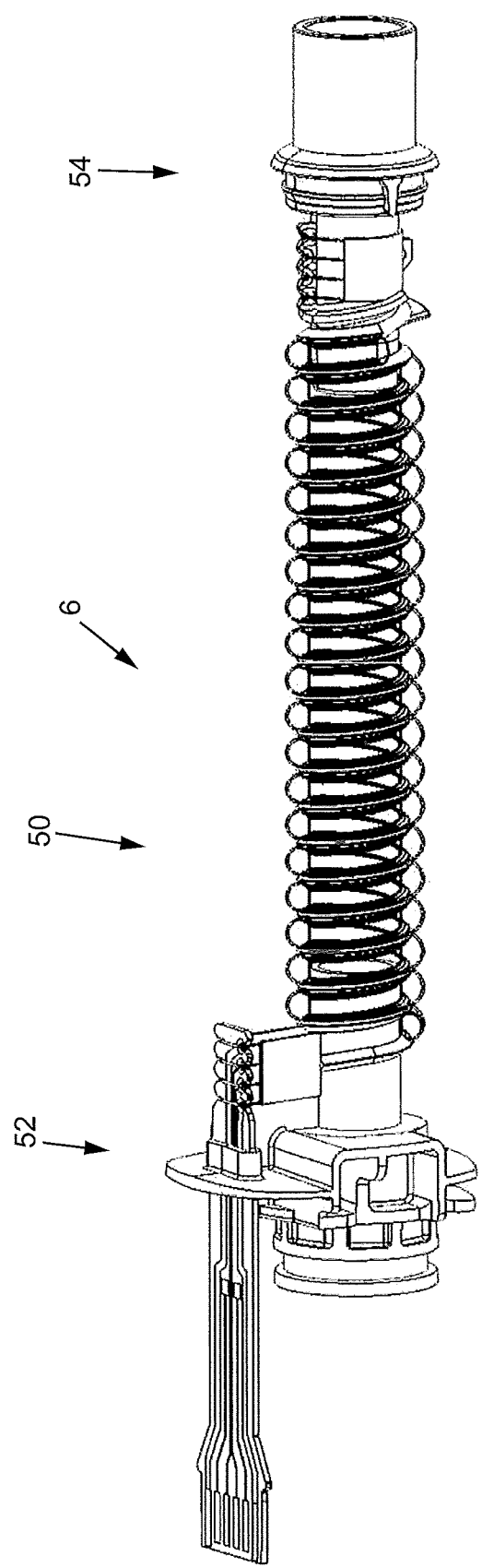

MEDICAL TUBES FOR RESPIRATORY SYSTEMS

INCORPORATION BY REFERENCE TO RELATED APPLICATIONS

Any and all applications for which a foreign or domestic priority claim is identified in the Application Data Sheet as filed with the present application are hereby incorporated by reference under 37 CFR 1.57. In addition, this application hereby incorporates by reference the entirety of the following applications:

U.S. Provisional Application No. 61/726,532, filed Nov. 14, 2012.
U.S. Provisional Application No. 61/786,141, filed Mar. 14, 2013.
U.S. Provisional Application No. 61/877,736, filed Sep. 13, 2013.
PCT/NZ2013/000208, filed Nov. 14, 2013.
U.S. Provisional Application No. 61/492,970, filed Jun. 3, 2011.
U.S. Provisional Application No. 61/610,109, filed Mar. 13, 2012.
PCT/IB2012/001786, filed May 30, 2012.
U.S. Provisional Application No. 61/733,360, filed Dec. 4, 2012.
U.S. Provisional Application No. 61/733,359, filed Dec. 4, 2012.
U.S. Provisional Application No. 61/877,622, filed Sep. 13, 2013.
U.S. application Ser. No. 14/123,485, filed Dec. 2, 2013.
PCT/NZ2013/000222, filed Dec. 4, 2013.
U.S. Provisional Application No. 61/877,784, filed Sep. 13, 2013.
U.S. Provisional Application No. 62/024,969, filed Jul. 15, 2014.
PCT/NZ2014/000201, filed Sep. 15, 2014.
U.S. Provisional Application No. 61/954,230, filed Mar. 17, 2014
U.S. Provisional Application No. 62/031,666, filed Jul. 31, 2014.
U.S. Provisional Application No. 62/047,536, filed Sep. 8, 2014.
U.S. Provisional Application No. 62/131,173, filed Mar. 10, 2015.

BACKGROUND

Field

The present disclosure generally relates to respiratory humidification systems. More particularly, the present disclosure relates to medical tubes for respiratory humidification systems.

Description of the Related Art

Respiratory systems are used to provide respiratory gases to a patient. A respiratory system may include a humidification device to condition the gases provided to a patient. These gases may be heated or humidified prior to delivery. Gases are delivered to a patient via a medical tube in fluid communication with a patient interface. Examples of a patient interface include an oral mask, a nasal mask, a nasal cannula, a tracheal mask, an endotracheal tube, or a combination of oral and nasal masks. Gases delivered to patients at 100% relative humidity and 37° C. mimic the properties resulting from the transformation of air that occurs as it passes through the nose to the lungs. This promotes efficient gas exchange and ventilation in the lungs, aids defense mechanisms in the airways and increases patient comfort during treatment. Medical tubes for delivering gases to a patient may have a wire, such as a heater wire to keep the heated, humidified gases warm and prevent condensate forming in the medical tube, or a sensor wire to convey data from a sensor in the medical tube. A connector may be used to form an electrical and/or pneumatic connection between the medical tube and a respiratory system component, such as a humidification device or a patient interface.

SUMMARY

Although connectors for connecting a medical tube to a respiratory system component exist in the prior art, certain features, aspects and advantages of at least one of the embodiments disclosed herein includes the realization that there are problems associated with connecting a medical tube to a respiratory system component. A medical tube may have a wire, such as a heater wire, a sensor wire, or any other type of electrical conductor. A wire may lie within the medical tube, or may be embedded in the wall of the medical tube, or may be positioned on the exterior of the medical tube. Other ways of including a wire in a medical tube may also be used. A medical tube may have an embedded wire in the wall of the medical tube to reduce or eliminate the likelihood of the wire being exposed to the gases flow. However, a wire may need to form an electrical connection to a respiratory system component through, or via, a connector, without affecting the pneumatic connection between the medical tube and the connector. It may be difficult to form a reliable connection between the medical tube with an embedded wire and a connector.

Embodiments are disclosed that provide a medical tube that is configured to connect to a connector in a way that provides solutions to the problems in the prior art. The medical tube may have one or more wires and may terminate at a connector. The connection between a medical tube and a connector may facilitate an electrical and pneumatic connection. A medical tube may comprise a first elongate member and a second elongate member. The one or more wires may be embedded in the second elongate member. The second elongate member may terminate with a flattened portion that exposes the one or more wires such that it can be attached to a connector. In some embodiments, the second elongate member may terminate with a flattened portion that exposes the one or more wires and have a second flattened portion that may aid attachment of the one or more wires to a connector.

In some configurations, a medical tube is configured to deliver respiratory gases to a patient. The medical tube comprises a first elongate member and a second elongate member. The second elongate member comprises one or more embedded wires. The second elongate member terminates at the end of the tube as a tail. The tail comprises a flattened portion and an exposed portion. The one or more wires is exposed in the exposed portion so as to form an electrical connection with a respiratory system component.

In some configurations, the electrical component is a connector that is configured to connect the medical tube to a respiratory system component.

In some configurations, the one or more wires comprises at least one heater wire and/or at least one sensing wire. In some such configurations, the at least one sensing wire is used to sense one of temperature, flow, humidity, or pressure.

In some configurations, the one or more wires comprises four wires.

In some configurations, the one or more wires comprises two heater wires and two sensing wires.

In some configurations, the tail comprises a second flattened portion following the exposed portion.

In some configurations, the spacing between each of the one or more wires is configured for attachment to the respiratory system component. For example, the one or more wires can be relatively more spaced in the exposed portion than in an unflattened portion of the second elongate member.

In some configurations, the spacing between each of the one or more wires is configured for attachment to a printed circuit board.

In some configurations, a connector is joined to an end of the tube. In some such configurations, the connector is at least one of a patient-end connector and a chamber-end connector.

In some configurations, the connector comprises a housing that is connected to the end of the tube. In some such configurations, the connector is configured to form an electrical and pneumatic connection between the medical tube and a respiratory system component. In some such configurations, the tail is connected to the connector. In some such configurations, the tail is connected to a printed circuit board. The printed circuit board can be supported by a housing. In some such configurations, the printed circuit board is integrated into a housing of the connector using overmolding. In some such configurations, the printed circuit board spans a diameter of a passage through the housing. In some such configurations, the printed circuit board is supported by a ledge that extends along a portion of the printed circuit board to which the one or more wires is soldered.

In some configurations, a comb is positioned on a first lateral side of the printed circuit board and the one or more wires is soldered adjacent to a second lateral side of the printed circuit board that is opposite of the first lateral side of the printed circuit board. In some such configurations, the second lateral side of the printed circuit board comprises notches that receive the one or more wires. In some configurations, an exposed portion of the one or more wires extends between the printed circuit board and the comb. In some configurations, the printed circuit board comprises pairs of notches that receive the one or more wires, each pair of notches comprises a notch on a first lateral side of the printed circuit board and a notch on a second lateral side of the printed circuit board, and each of the one or more wires is soldered to one of each pair of notches. In some such configurations, at least one of the one or more wires is soldered to a notch on the first lateral side of the printed circuit board and at least one of the one or more wires is soldered to a notch on the second lateral side of the printed circuit board. In some configurations, buttresses extend outward from the ledge at locations defined between the notches on the second lateral side of the printed circuit board.

In some configurations, the one or more wires comprise two sensing wires and two heater wires and four attachment features are positioned on one lateral side of the printed circuit board. In some such configurations, the sensing wires are soldered to an inner two of the four attachment features, and the heater wires are soldered to an outer two of the four attachment features. In some configurations, the one or more wires comprises at least one heater wire and at least one sensor wire, the at least one heater wire is soldered to a notch of one of the first and second lateral sides of the printed circuit board, and the at least one sensor wire is soldered to a notch of the other of the first and second lateral sides of the printed circuit board. In some configurations, the one or more wires comprises at least one heater wire and at least one sensor wire, the at least one heater wire is soldered to an attachment feature on a first side or face of the printed circuit board, and the at least one sensor wire is soldered to an attachment feature on an opposite second side or face of the printed circuit board.

In some configurations, at least a portion of the tail can be positioned between a cover and a surface of the housing. In some such configurations, the cover is hingedly connected to the housing. In some such configurations, the cover has a curved inner surface that complements the surface of the housing. In some configurations, the cover comprises one or more retention members. In some configurations, the one or more retention members secure the cover to the housing. In some such configurations, the one or more retention members secure the cover to the ledge. In some such configurations, the one or more retention members secure the cover along an edge of the cover. In some configurations, the one or more retention members secure the cover to a post. In some configurations, the second flattened portion of the tail is positioned between the cover and the surface of the housing.

In some configurations, a juncture between the medical tube and the housing is covered with an overmold material. In some such configurations, the overmold material also covers an electrical connection between the medical tube and the housing. In some such configurations, the overmold material seals the first elongate member.

In some configurations, the overmold material at least partially melts the second elongate member.

In some configurations, the overmold material at least partially melts the first elongate member.

In some configurations, the housing comprises one or more external features that guide a connection of the tube to the housing. In some such configurations, the one or more external features comprise a helical rib. In some configurations, the helical rib does not completely surround the housing. In some configurations, a pitch of the helical rib corresponds to a pitch of the first elongate member and applies pressure to the first elongate member when the medical tube is connected to the housing. In some such configurations, the one or more external features comprises a guidance tab. In some such configurations, the one or more external features comprises a drift limit post.

In some configurations, the tail comprises an unflattened portion between an end of the first elongate member and the flattened portion, and the overmold material covers a juncture between the medical tube and the housing of the connector. In some such configurations, the overmold material at least partially surrounds the unflattened portion. The connector can comprise a bridge, and the unflattened portion can be configured to extend over the bridge such that the bridge is configured to lift the unflattened portion away from the housing. In some such configurations, a drift limit post is positioned at one end of the bridge. In some configurations, the connector comprises a helical rib having a first end, a second end, and a longitudinal bridge connecting the first end and the second end, and the helical rib and bridge are configured to act as a liquid barrier. In some such configurations, the unflattened portion is configured to extend over the longitudinal bridge such that the bridge lifts the unflattened portion away from the housing. In some configurations, a bridge configured to lift the unflattened portion away from the housing comprises a pad coupled to the housing. In some configurations, the housing comprises a recessed portion, and the unflattened portion is configured to extend over the recessed portion. In some configurations, the connector comprises a channel axially cut into the housing, and the unflattened portion is configured to extend over the channel.

In some configurations, the overmold material that covers a juncture between the medical tube and the housing of the connector is configured to bond to the first elongate member, the second elongate member, the body of the connector, the printed surface board, and the exposed portion of the one or more wires. In some such configurations, the connector housing comprises polypropylene. The first and second members of the medical tube can comprise polyolefin elastomers. In some configurations, the printed circuit board comprises a plasma-treated glass-reinforced epoxy-laminate. In some configurations, the overmold material comprises an ethylene copolymer and methylacrylate.

BRIEF DESCRIPTION OF THE DRAWINGS

These and other features, aspects, and advantages of the present disclosure will be described with respect to the following figures, which are intended to illustrate and not to limit the preferred embodiments.

FIG. 7A is a perspective view of a tube assembly having a single conduit segment and a connector at each end.

DETAILED DESCRIPTION OF THE PREFERRED EMBODIMENT

Figure 1:
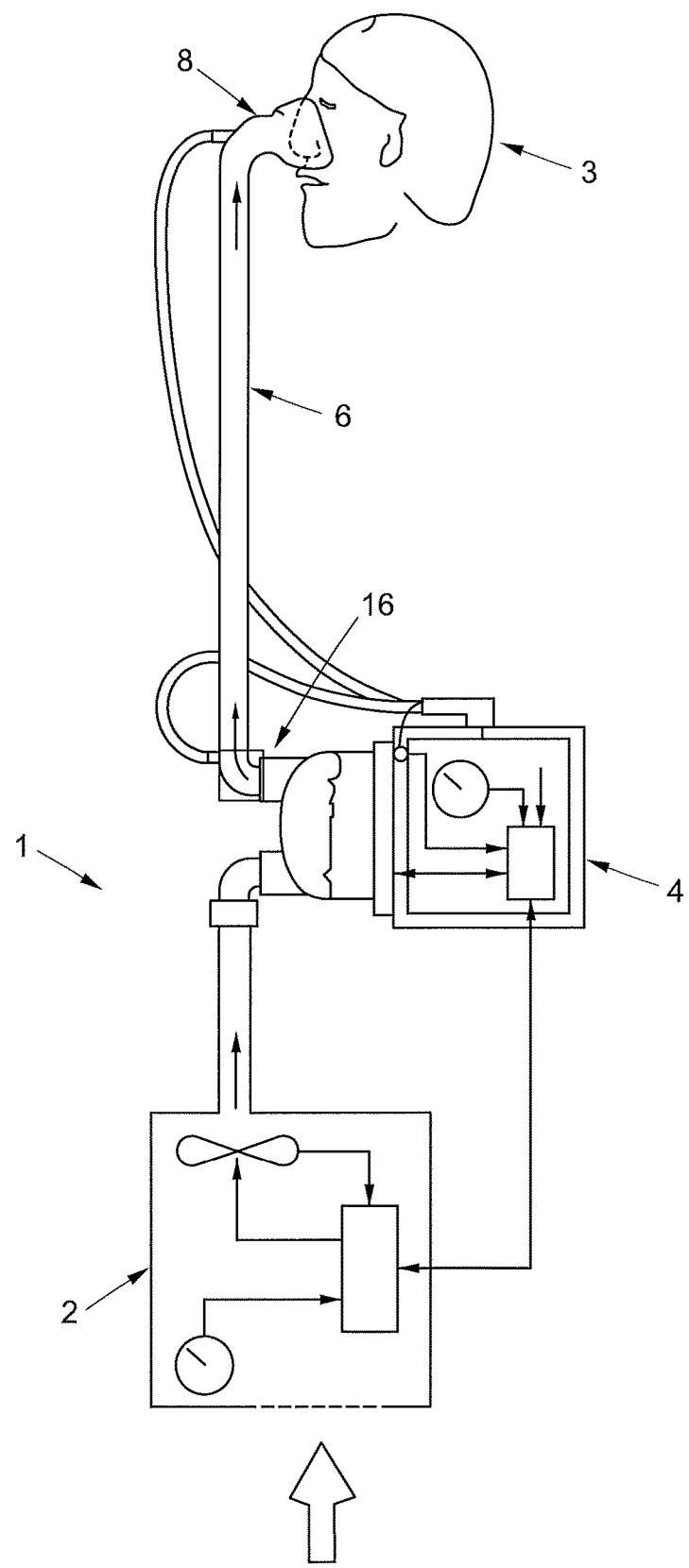
FIG. 1 is a schematic of a respiratory system to deliver respiratory gases to a patient.

FIG. 1 shows a respiratory system 1 which can include, but is not limited to, the following components: a pressurized gases source 2, such as a blower or ventilator, adapted to generate a supply of gases to be delivered to a patient 3; a humidification device 4 adapted to condition the supply of gases; a medical tube 6 adapted to deliver the gases to a patient interface 8, which then delivers the gases to the patient 3; and a connector 16 adapted to connect the medical tube 6 to the humidification device 4.

The patient interface 8 as described herein may refer to a mask, nasal mask, nasal prongs, oral mask, tracheal mask, or nasal pillows.

The humidification device 4 as described herein may refer to any device that conditions gases. This may include heating the gases and/or humidifying the gases.

Gases as described herein may refer to air, oxygen, carbon dioxide, or a mixture of any such gases, or a combination of any such gases with one or more medicaments or aerosols that may be delivered to the patient 3 via the patient interface 8.

Figure 2:
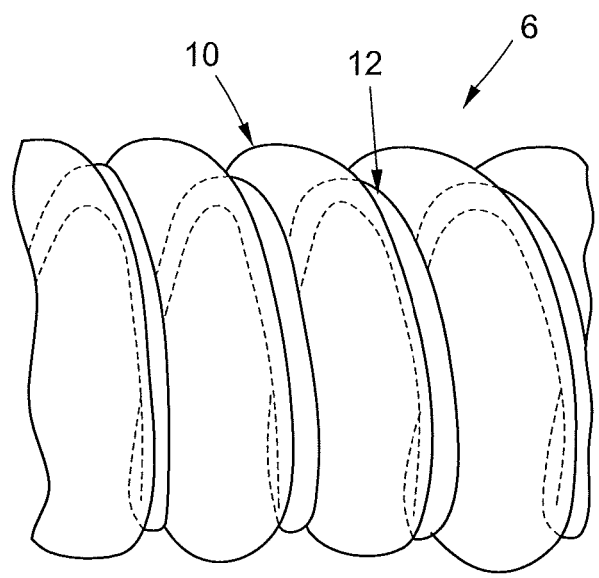
FIG. 2 is a perspective view of a medical tube.
Figure 5:
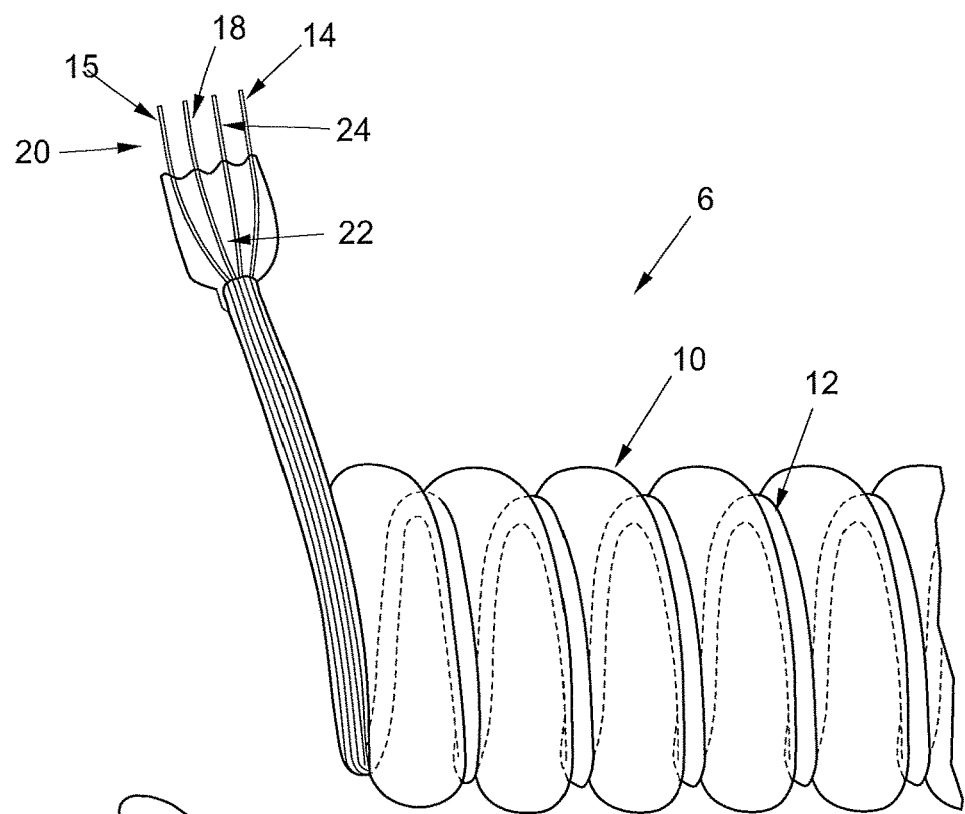
FIGS. 5 and 6 are perspective views of a medical tube with different embodiments of the termination of a medical tube to aid connection to a respiratory system component.
Figure 6:
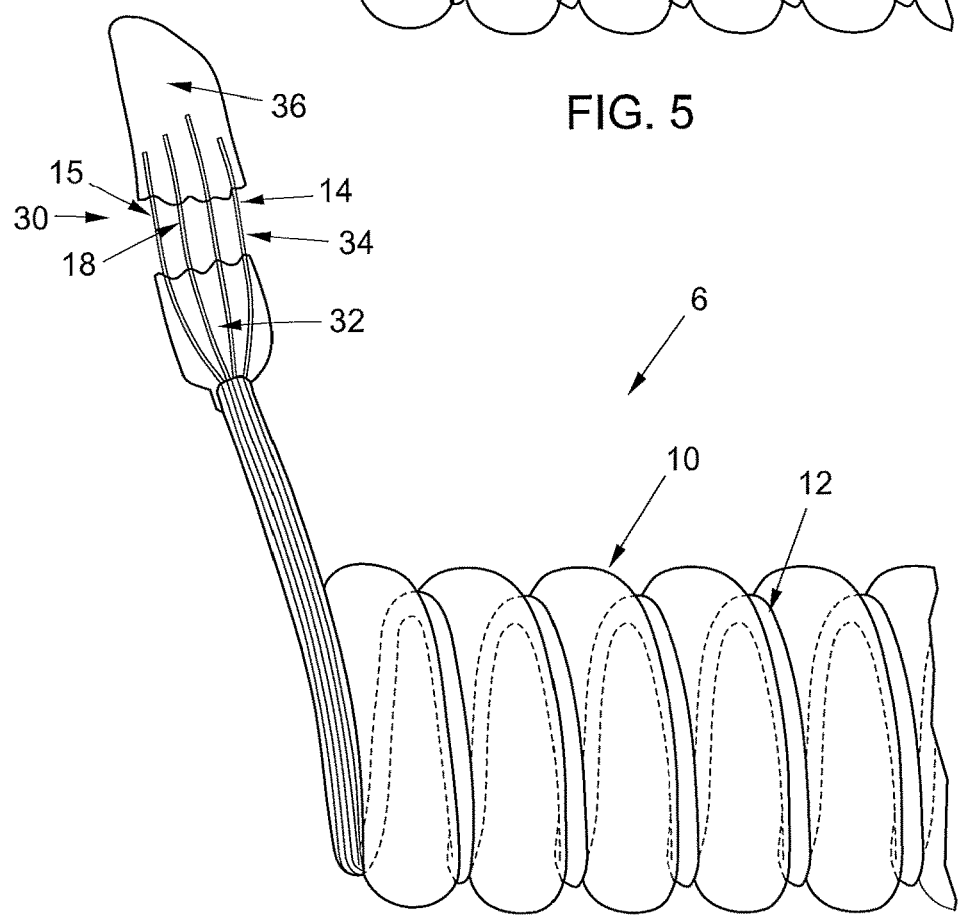

The medical tube 6 as described herein may refer to a tube, conduit, circuit, or hose. In FIGS. 2, 5, and 6, the medical tube 6 illustrated may comprise a first elongate member 10 and a second elongate member 12. In FIGS. 5 and 6, the medical tube 6 illustrated may comprise one or more wires 15. The one or more wires 15 may comprise at least one heater wire, at least one sensor wire, and/or any other type of electrical conductor. The one or more wires 15 may be within the medical tube 6. The one or more wires 15 may be lying along an inner or outer surface of the medical tube 6. The one or more wires 15 may be spirally wound onto the medical tube 6 or into the medical tube 6 such that the one or more wires 15 may be embedded in the wall of the medical tube 6.

The medical tube 6 may be heated or unheated. The medical tube 6 may include insulation to reduce condensate from forming within the medical tube 6. In some embodiments, the first elongate member 10 may provide such insulation. Condensate may form if the heated, humidified gases within the medical tube 6 cool down during transit. To reduce or eliminate condensate formation, the medical tube 6 may be heated. This heating may be provided by the one or more wires 15 comprising one or more heater wires 14, as shown in FIGS. 5 and 6. In some embodiments, the second elongate member 12 may comprise the one or more wires 15.

A terminating portion of the medical tube 6 may be provided to terminate the one or more wires 15 at the connector 16 such that an electrical connection may be formed between the medical tube 6 and a component of the respiratory system 1. In some embodiments, the terminating element may comprise a tail 20 or a tail 30, as illustrated in relation to the medical tube 6 in FIGS. 5 and 6, and also as illustrated close up in FIGS. 3 and 4. The connector 16 may provide a pneumatic connection between the medical tube 6 and a component of the respiratory system 1. A component of the respiratory system 1 as described herein may refer to a patient interface or a humidification device. The connector 16 may provide either one of or both an electrical and pneumatic connection between the medical tube 6 and a component of the respiratory system 1.

The one or more wires 15 may also comprise one or more sensing wires 18, as illustrated in FIGS. 5 and 6. The one or more sensing wires 18 may be used to sense gases properties such as temperature, flow, humidity, or pressure. In some embodiments, the one or more sensing wires 18 may be used to sense temperature. In some embodiments, the one or more sensing wires 18 may be connected to one or more sensors that may be used to sense one or more of these gases properties.

In some embodiments, as shown in FIGS. 5 and 6, the one or more wires 15 are embedded in the medical tube 6. In some embodiments, the one or more wires 15 may be embedded in the second elongate member 12. In some embodiments, the one or more wires 15 may be embedded in the first elongate member 10. In some embodiments, both the one or more heater wires 14 and the one or more sensing wires 18 may be embedded in the second elongate member 12. In some embodiments, both the one or more heater wires 14 and the one or more sensing wires 18 may be embedded in the first elongate member 10. In some embodiments, at least one of the one or more heater wires 14 and the one or more sensing wires 18 may be embedded in the second elongate member 12, and at least one other of the one or more heater wires 14 and the one or more sensing wires 18 may be embedded in the first elongate member 10. In some embodiments, there may be no heater wires 14 within the second elongate member 12. In some embodiments, there may be no sensing wires 18 within the second elongate member 12. There may be any other such combination.

In some embodiments, the one or more heater wires 14 may comprise two heater wires. In some embodiments, the one or more sensing wires 18 may comprise two sensing wires. In some embodiments, the one or more sensing wires 18 may be located near the one or more heater wires 14. In some embodiments, the one or more heater wires 14 may comprise a first heater wire and a second heater wire, and the one or more sensing wires 18 may be located between the first heater wire and the second heater wire.

The first elongate member 10 and the second elongate member 12 may be made from different materials. For example, the first elongate member 10 may be flexible and/or may provide thermal insulation properties to the medical tube 6. The second elongate member 12, for example, may be made from material that provides reinforcing properties and/or structural support to the medical tube 6. In some embodiments, the first elongate member 10 may provide reinforcing properties and/or structural support for the medical tube 6. In some embodiments, the second elongate member 12 may be flexible and/or may provide thermal insulation properties. Different combinations may also be provided. In some embodiments, the medical tube 6 may comprise a single elongate member. In some embodiments, the medical tube 6 may comprise two or more first elongate members. In some embodiments, the medical tube 6 may comprise two or more second elongate members.

In some embodiments, the tails 20, 30 may extend from the second elongate member 12, as illustrated in FIGS. 5 and 6. In some embodiments, the tails 20, 30 may extend from the first elongate member 10. In some embodiments, the tails 20, 30 may extend from a combination of the first elongate member 10 and the second elongate member 12. Similarly, if greater than two elongate members are used, the tails 20, 30 may extend from any one of or from more than one elongate member in the system. The tails 20, 30 as described herein refer to terminating portions of the first elongate member 10 and/or the second elongate member 12 that have been adapted to enable connection of the first elongate member 10 and/or the second elongate member 12 to an electrical component. An electrical component may refer, for example, to a printed circuit board or an electrical connector.

Figures 3, 4:
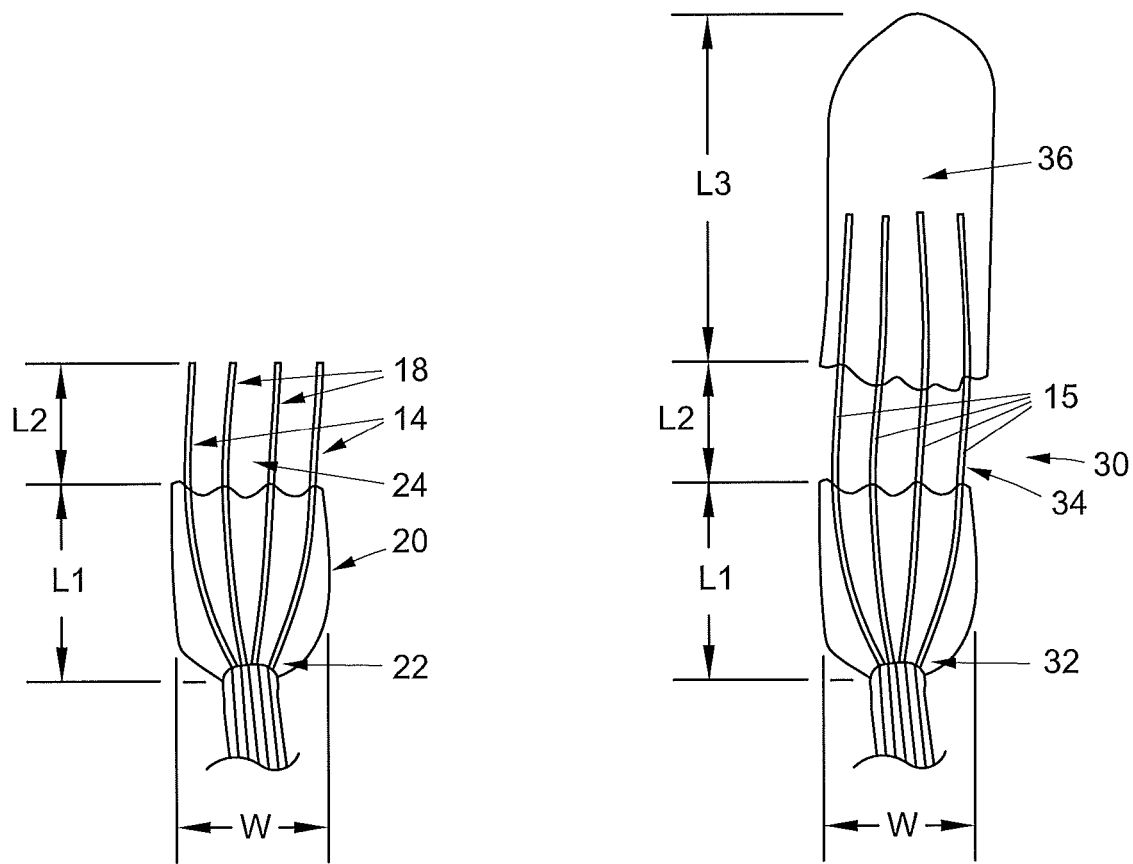
FIGS. 3 and 4 are perspective views of different embodiments of the termination of a medical tube to aid connection to a respiratory system component.

As illustrated in FIGS. 3 and 5, the tail 20 may comprise a flattened portion 22 and an exposed portion 24. In some embodiments, the tail 20 may comprise a transition or preliminary portion, between the first elongate member 10 and/or the second elongate member 12 and the flattened portion 22, that is not flattened or is less flattened than the flattened portion 22. As illustrated in FIGS. 4 and 6, the tail 30 may comprise a first flattened portion 32, an exposed portion 34, and a second flattened portion 36. In some embodiments, the tail 30 may comprise a transition or preliminary portion, between the first elongate member 10 and/or the second elongate member 12 and the first flattened portion 32, that is not flattened or is less flattened than the first flattened portion 32. In some embodiments, the tails 20, 30 may comprise only the exposed portions 24, 34, respectively; however, the flattened portion 22, the first flattened portion 32, and/or the second flattened portion 36 may aid in handling and connection of the one or more wires 15 to an electrical component. The flattened portion 22 and/or the first flattened portion 32 may be made from the same material as the second elongate member 12. In some embodiments, the width W of the flattened portion 22, the first flattened portion 32, and/or the second flattened portion 36 may be at most 11.0 mm, at most 9.0 mm, or at most 8.5 mm. In some embodiments, the length L1 of the flattened portion 22 and/or the first flattened portion 32 may be at least 8.0 mm. In some embodiments, the length L2 of the exposed portion 24 and/or the exposed portion 34 may be at least 8.0 mm or at least 10.0 mm. In some embodiments, the length L3 of the second flattened portion 36 may be at least twice the length of the exposed portion 34, at most 32.0 mm, or at most 25.0 mm.

The flattened portion 22 describes a portion of the tail 20, and the first flattened portion 32 describes a portion of the tail 30, wherein the one or more wires 15 may become spaced. Spacing as herein described may refer to the separation or moving apart of the one or more wires 15, and may refer to the location and position of the one or more wires 15 within the flattened portion 22, the first flattened portion 32, and/or the second flattened portion 36. If the one or more wires 15 comprises more than one wire—such as two or more heater wires, a combination of at least one heater wire and at least one sensing wire, two or more sensing wires, or any other combination of electrical conductors—then each of the one or more wires 15 may be spaced relative to each other. This spacing may be to aid attachment of the one or more wires 15 to an electrical component. This spacing may be determined by the width of the flattened portion 22 and/or the first flattened portion 32. In some embodiments, the spacing between each of the one or more wires 15 may be 2.5 mm, at most 4.0 mm, or at least 1.0 mm. In some configurations, the distance between any two outermost wires may be less than 9.0 mm or less than 8.0 mm A range of separation or spacing distances between each of the one or more wires 15 may be used.

Once the one or more wires 15 have been spaced, the flattened portion 22 and/or the first flattened portion 32 may extend beyond either side of the one or more wires 15. The flattened portion 22 and/or the first flattened portion 32 may encase the one or more wires 15. The amount of the flattened portion 22 and/or the first flattened portion 32 encasing the one or more wires 15 may be within a range of values. In some embodiments, the flattened portion 22 and/or the first flattened portion 32 may extend by 0.25 mm on either side of the one or more wires 15. The flattened portion 22 and/or the first flattened portion 32 may extend on either side of the one or more wires 15 by more, or less, as required.

The flattened portion 22 and the first flattened portion 32 of the second elongate member 12 may be formed using known flattening techniques. The length of the flattened material may be important with regard to spacing and to maintaining the spacing of the one or more wires 15. If the one or more wires 15 comprises more than one wire, the length of the flattened material that forms the flattened portion 22 and the first flattened portion 32 may help to space each of the one or more wires 15 relative to each other. Each of the one or more wires 15 may be spaced relative to each other before they are exposed. In some embodiments, the one or more wires 15 may be spaced relative to each other after they have been exposed. In some embodiments, each of the one or more wires 15 may be spaced from each other as they are exposed. Spacing of each of the one or more wires 15 relative to each other may reduce the likelihood that the order of the one or more wires 15 will be confused. This may aid an assembly operator with regards to usability and handling. The spacing between the wires can be as described above.

The exposed portions 24, 34 may be discrete portions that follow the flattened portion 22 or the first flattened portion 32, respectively. The one or more wires 15 may be exposed in the exposed portions 24, 34. The length of the exposed portions 24, 34 may be important. The exposed portions of the one or more wires 15 may be attached to an electrical component. Any suitable method to expose a portion of the flattened portion 22 and/or the first flattened portion 32 may be used. The exposed portions 24, 34 may have lengths that facilitate attachment of the one or more wires 15 to an electrical component.

FIGS. 4 and 6 show embodiments in which the second flattened portion 36 may be used to facilitate attachment of the second elongate member 12 to an electrical component. The second flattened portion 36 may be located away from or at the other end of the exposed portion 34 relative to the first flattened portion 32. The second flattened portion 36 may cover the one or more wires 15 and may extend beyond the length of the one or more wires 15. The second flattened portion 36 may be useful in attaching the second elongate member 12 to an electrical component. For example, the second flattened portion 36 may facilitate wrapping of the tail 30 around an electrical component and/or a connector, such as the connector 16. The second flattened portion 36 may also further maintain the spacing of the one or more wires 15 within the tail 30. The second flattened portion 36 may be made using the same material as the second elongate member 12. In some embodiments, the second flattened portion 36 may be made using a different material. The second flattened portion 36 may aid handling of the one or more wires 15. For example, it may not be necessary to handle each of the one or more wires 15 individually, which may improve the efficiency of assembling the medical tube 6 to a connector, such as the connector 16. In some embodiments, the second flattened portion 36 may be unused. Other mechanisms or techniques to maintain the positioning and spacing of the one or more wires 15 could be used.

An electrical component may be attached to the one or more wires 15. The electrical component may be connected to the medical tube 6 by, for example, overmolding or adhesive, or by using a clipping mechanism. The connector 16 may form a connection between the medical tube 6 and an electrical component or another component of the respiratory system 1. In some embodiments, the connector 16 may form a connection between the medical tube 6 and the humidification device 4. In some embodiments, the connector 16 may form a connection between the medical tube 6 and the patient interface 8. The connector 16 may also be used to form a connection between the medical tube 6 and the blower 2. In some embodiments, the connector 16 may be used to form an electrical and pneumatic connection between the medical tube 6 and at least one other medical tube. The medical tube 6 may be for infant, paediatric, or adult use. In some embodiments, the medical tube 6 may be connected pneumatically to at least one other medical tube. In some embodiments, the one or more wires 15 may be terminated at the connector 16 without forming an electrical connection. The tails 20, 30 may still be used in these embodiments to aid in connecting the medical tube 6 to the connector 16. In some embodiments, the tails 20, 30 may be unused or may be omitted. In some embodiments, known ways to attach the medical tube 6 to the connector 16 may be used. Hence, the connector 16 is not limited to the connections it may form, and other connections between a medical tube and a component of the respiratory system 1 may be arranged and configured in accordance with certain features, aspects and advantages of the present disclosure.

A housing of the connector 16 may be formed from a transparent material. The transparent material may allow an operator to assess if the one or more wires 15 have been separated and/or positioned correctly on the connector 16. In some embodiments, the housing of the connector 16 may be a coloured material. In some embodiments, the housing of the connector 16 may be an opaque material, such that a user may be unable to see through the material.

Figure 7:
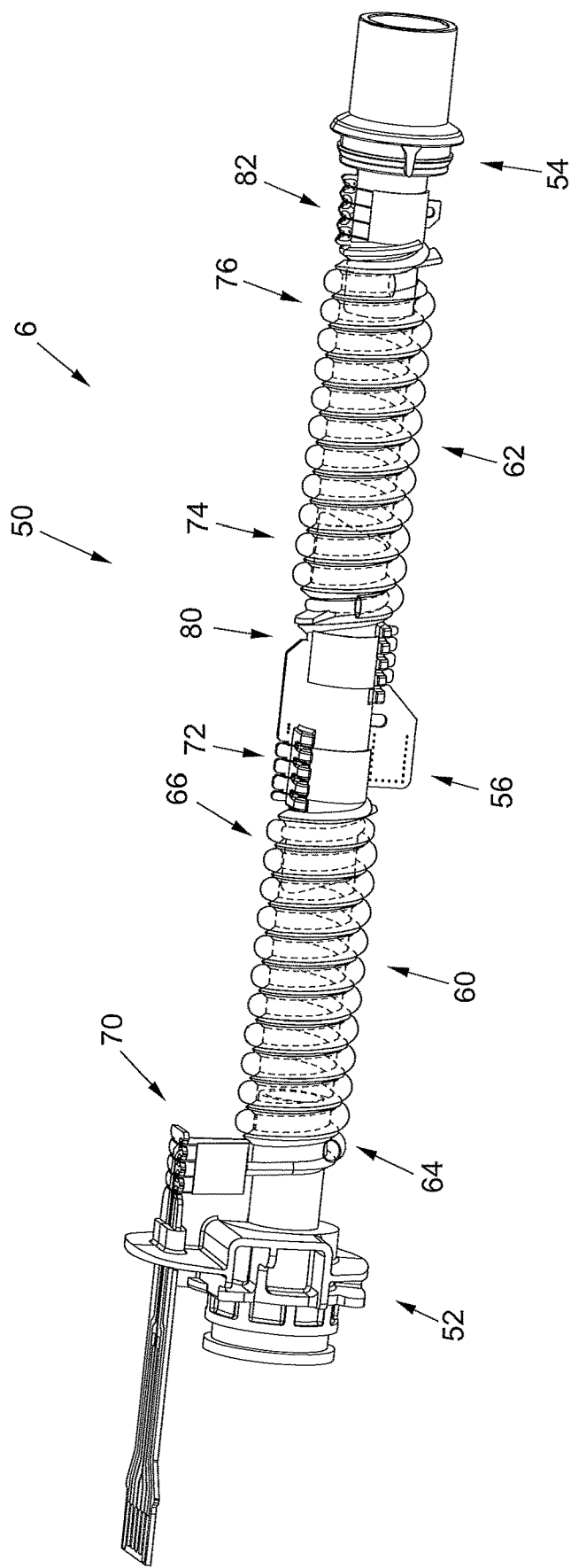
FIG. 7 is a perspective view of a tube assembly employing connections between two conduit segments, in which the connections are established by connectors that are shown without outer covers for clarity.

With reference now to FIG. 7, the tube 6 is illustrated in a configuration that defines a breathing tube 50. The illustrated breathing tube 50 has a chamber-end connector 52 and a patient-end connector 54. The chamber-end connector 52 can be configured as described in PCT/NZ2014/000201, filed Sep. 15, 2014 and PCT/NZ2013/000222, filed Dec. 4, 2013, each of which is hereby incorporated by reference in its entirety. The patient-end connector 54 can be configured as described in PCT/NZ2013/000208, filed Nov. 14, 2013 and PCT/NZ2013/000222, filed Dec. 4, 2013, each of which is hereby incorporated by reference in its entirety. In some configurations, as in the illustrated configuration, the breathing tube 50 also comprises an intermediate connector 56. The intermediate connector 56 can be configured as described in PCT/NZ2013/000208, filed Nov. 14, 2013 and PCT/NZ2013/000222, filed Dec. 4, 2013, each of which is hereby incorporated by reference in its entirety. While illustrated without outer covers, each of the connectors 52, 54, 56 can comprise suitable outer covers, for example as shown and described in FIGS. 10A, 11C, and 14F and the associated description, to provide an aesthetically pleasing outer appearance, to provide ergonomic outer surfaces for gripping or other manipulations, and to enshroud the components that define the electrical, mechanical, and pneumatic junctures described herein. In some configurations, the breathing tube 50 comprises more than one intermediate connector 56; other configurations of the intermediate connector 56 may be used.

In some configurations, the intermediate connector 56 joins a first tube segment 60 and a second tube segment 62. The first tube segment 60 can be connected to the chamber-end connector 52 and the second tube segment 62 can be connected to the patient-end connector 54. When these components are secured together, an electrical path extends from the chamber-end connector 52 through the first tube segment 60 to the intermediate connector 56, across the intermediate connector 56, and from the intermediate connector 56 through the second tube segment 62 and to the patient-end connector 54. In effect, an unbroken electrical connection extends from the chamber-end connector 52 to the patient-end connector 54. Similarly, a pneumatic path extends from the chamber-end connector 52 through the first tube segment 60 to the intermediate connector 56, through the intermediate connector 56, and from the intermediate connector 56 through the second tube segment 62 and to the patient-end connector 54. In effect, an unbroken pneumatic connection extends from the chamber-end connector 52 to the patient-end connector 54. An unbroken pneumatic connection can also extend from a pneumatic component (e.g., a humidifier chamber, not shown) connected to the chamber-end connector 52 through to a pneumatic component (e.g., a patient interface, not shown) connected to the patient-end connector 54. In effect, these components combine together to define a single medical tube that comprises two or more segments.

The first tube segment 60 comprises a first end 64 and a second end 66. In some configurations, at least one of the first end 64 and the second end 66 comprises a tail 70. In some configurations, the first end 64 comprises the tail 70 while the second end 66 also comprises a tail 72. The tails 70, 72 can have any suitable configuration, including any of the configurations embodied by tails 20, 30.

Similarly, the second tube segment 62 comprises a first end 74 and a second end 76. In some configurations, at least one of the first end 74 and the second end 76 comprises a tail 80. In some configurations, the first end 74 comprises the tail 80 while the second end 76 also comprises a tail 82. The tails 80, 82 can have any suitable configuration, including any of the configurations embodied by tails 20, 30.

Figure 7B:
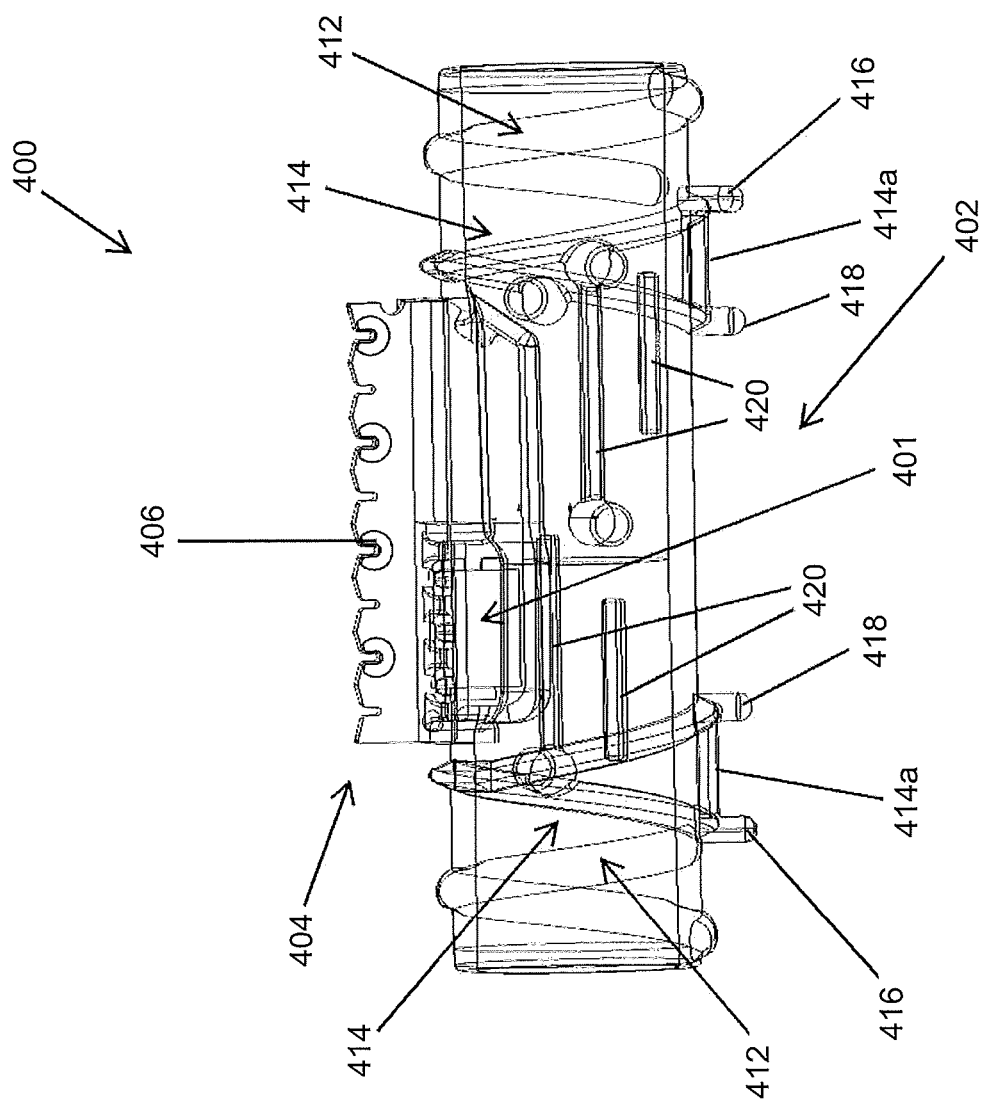
FIGS. 7B-7D illustrate an example embodiment of a midpoint assembly that can be used to join two conduit segments.
Figure 7C:
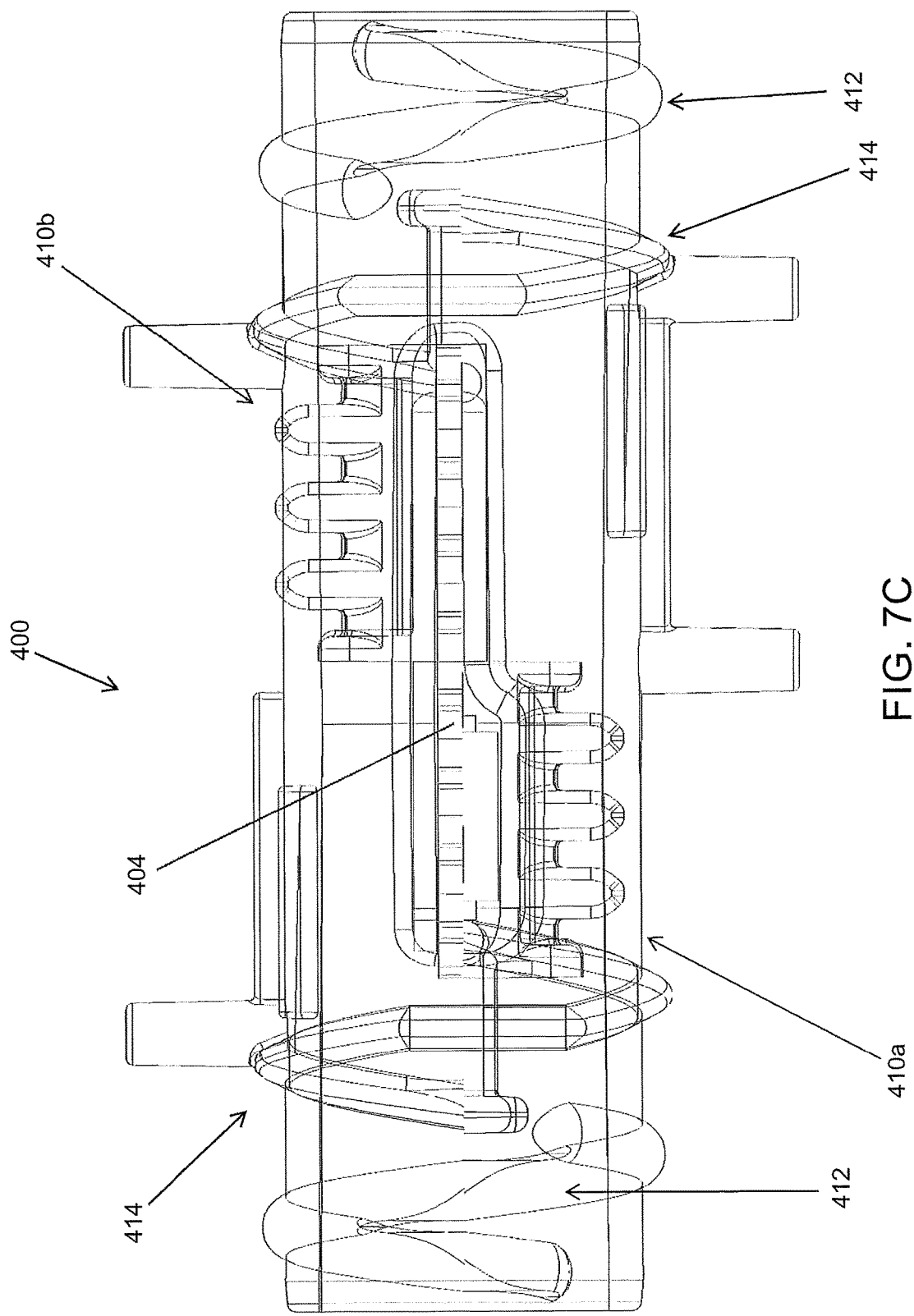
Figure 7D:
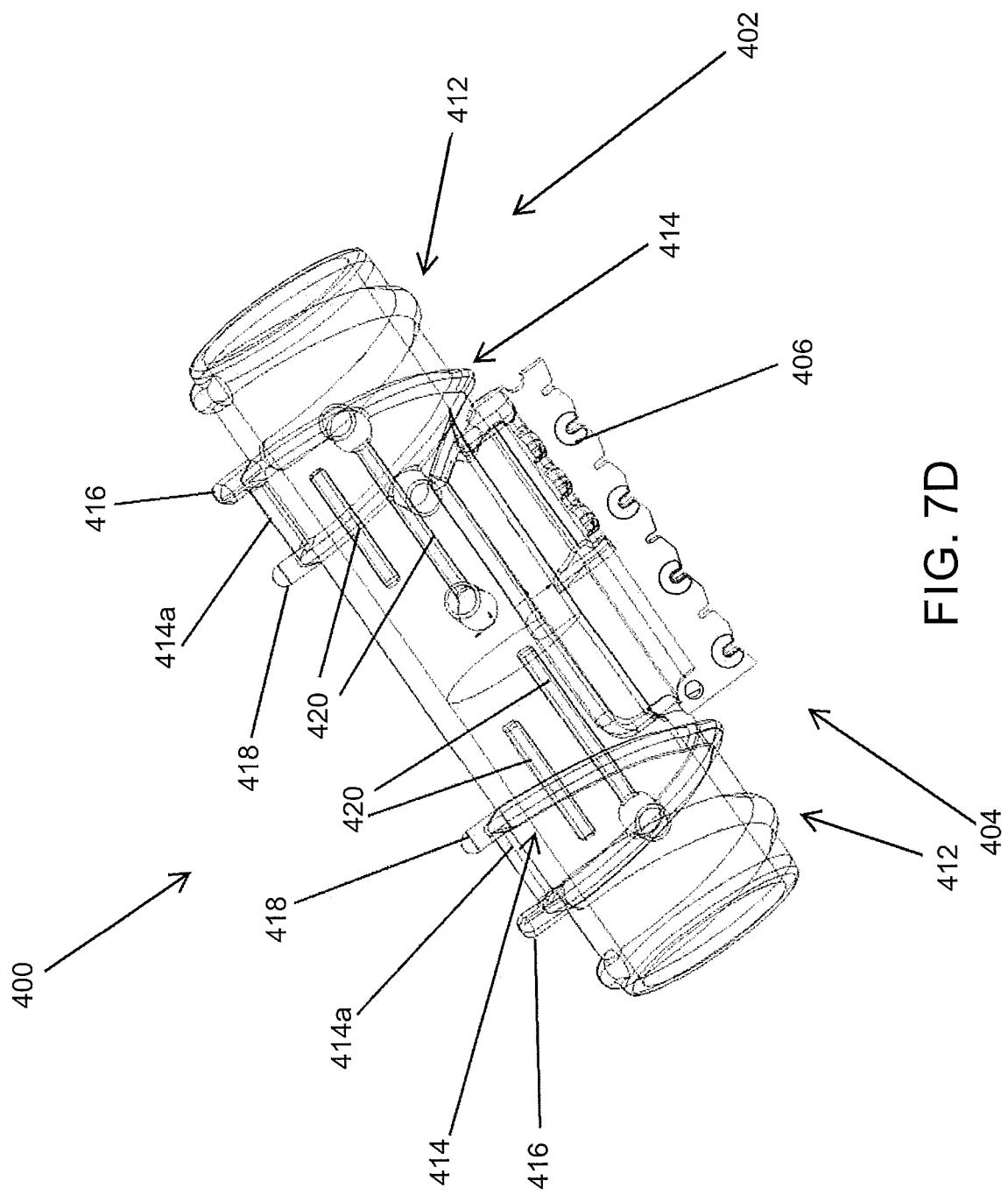

In some configurations, for example as illustrated in FIG. 7A, the tube 6 in a configuration that defines a breathing tube 50 may comprise a chamber-end connector 52 and a patient-end connector 54, but does not comprise an intermediate connector. In yet other embodiments, the tube 6 in a configuration that defines a breathing tube 50 can comprise a chamber-end connector 52, a patient-end connector 54, and a midpoint assembly. An example embodiment of a midpoint assembly 400 is shown in FIGS. 7B-7D. Additional details regarding the midpoint assembly 400 are discussed below.

Figure 8:
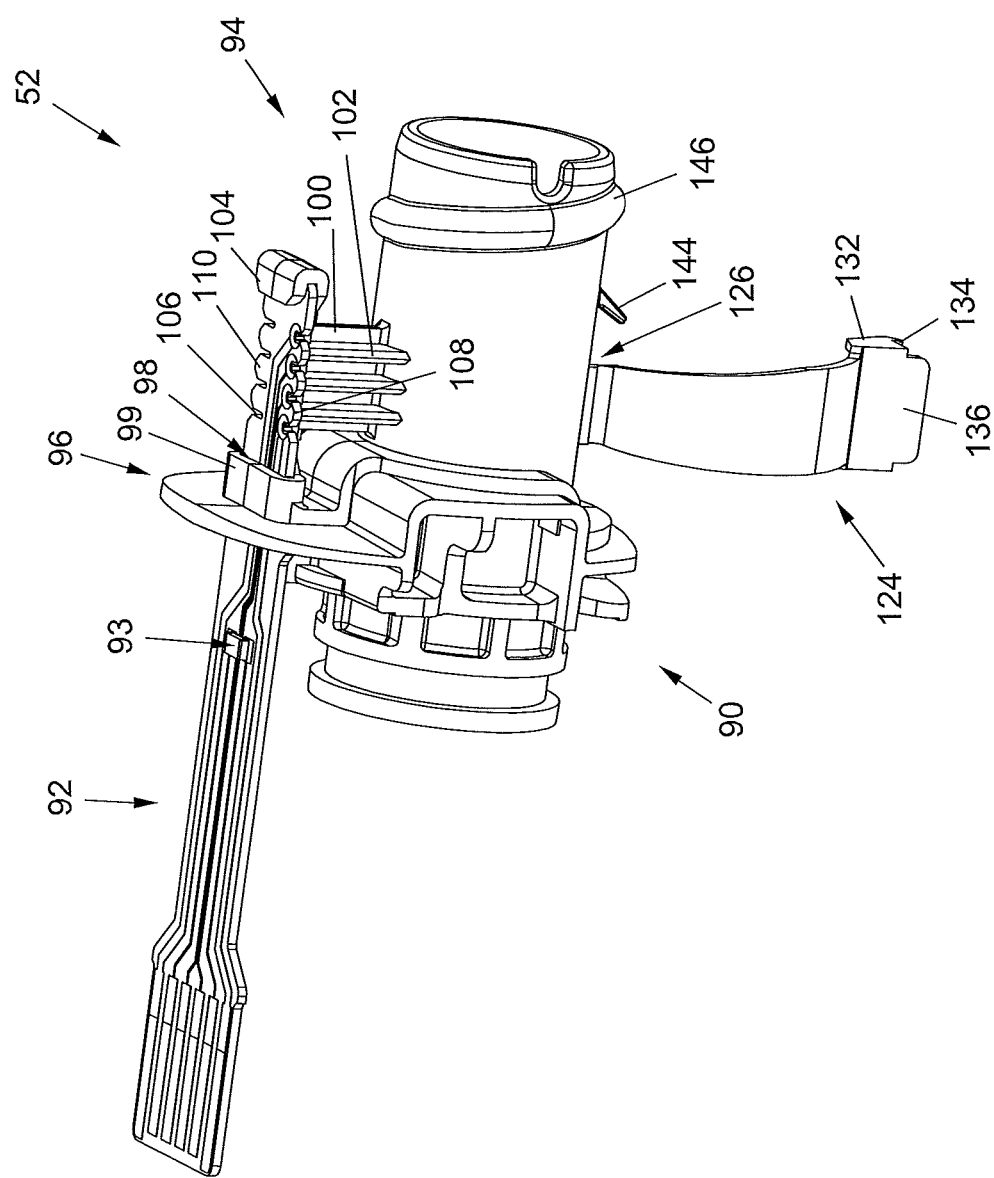
FIGS. 8-10A are perspective views of a portion of a chamber-end connector and an end of a conduit.

With reference now to FIG. 8, a portion of the chamber-end connector 52 is illustrated. In particular, the chamber-end connector 52 is illustrated without outer covers or housings. The chamber-end connector 52 comprises a plug portion 90. The plug portion 90 can support a printed circuit board or PCB 92.

The plug portion 90 comprises a main body 94. The main body 94 can be generally cylindrical. A mounting flange 96 can extend away from the main body 94. The mounting flange 96 can extend outward from the main body 94. The mounting flange 96 can define structure onto which the outer covers or housings can connect. In the illustrated configuration, the mounting flange 96 defines a passage 98 through which the printed circuit board 92 can extend. In the illustrated configuration, a shroud 99 extends from the mounting flange 96 and generally forms an extension of the passage 98 through with the PCB 92 extends.

Adjacent to the passage 98, a support ledge 100 can be formed. The support ledge 100 is arranged and configured to underlie the printed circuit board 92. In some configurations, the support ledge 100 extends radially outward from the main body 94. In some configurations, the support ledge 100 is an axially extending ridge that extends radially outward from the main body 94. In some configurations, the support ledge 100 is connected to the mounting flange 96.

In some configurations, the support ledge 100 can be reinforced by one or more buttresses 102. In the illustrated configuration, the support ledge 100 is reinforced by three buttresses 102. In the illustrated configuration, all of the buttresses 102 extend outward from a single side of the support ledge 100.

In some configurations, the support ledge 100 can comprise an upturned hook 104. The upturned hook 104 can turn back toward the mounting flange 96. The upturned hook 104 is arranged and configured to overlie at least a portion of the printed circuit board 92. In some configurations, a protrusion can be positioned inside of the upturned hook 104, which protrusion extends in an axial direction and which protrusion can be received within a recess defined on the axial end of the printed circuit board 92. In some configurations, the upturned hook 104 has a larger lateral dimension than the support ledge 100. In some configurations, the upturned hook 104 and a portion of the support ledge 100 underlying the upturned hook 104 both have a larger lateral dimension than a portion of the support ledge 100 not underlying the upturned hook 104. In some configurations, the upturned hook 104 extends from an axial end of the support ledge 100.

As illustrated, the printed circuit board 92 comprises one or more solder pads 106. As illustrated, the printed circuit board 92 can comprise attachment notches 108 that are at least partially surrounded by the solder pads 106. The attachment notches 108 can have any suitable configuration. In the illustrated configuration, the attachment notches 108 are positioned at locations that correspond to gaps positioned between the buttresses 102. In some configurations, the attachment notches 108 are positioned at locations that align with the gaps defined between the buttresses 102 when the end of the printed circuit board 92 is seated within the upturned hook 104.

The printed circuit board 92 can also comprise wire alignment components, such as alignment notches 110, for example but without limitation. In some configurations, as illustrated in FIG. 8, the attachment notches 108 are on one side of the printed circuit board 92 and the alignment notches 110 are on the opposite side of the printed circuit board 92. The alignment notches 110 can receive wires of the tail 70. The alignment notches 110 can generally align with the locations of the attachment notches 108. The alignment notches 110 can help to reduce or eliminate the likelihood of wires of the tail 70 crossing each other and can help to maintain wires of the tail 70 taut during soldering to the printed circuit board 92. In some configurations, two or more of the alignment notches 110 can be separated by a greater distance than the separation distance between the corresponding attachment notches 108, causing wires of the tail 70 to fan out from the attachment notches 108 to the alignment notches 110 in order to improve access for soldering and to further reduce the likelihood of wires of the tail 70 crossing each other. The alignment notches 110 can be sized and configured to accommodate wires of the tail 70. While the alignment notches 110 are illustrated as a portion of the printed circuit board 92, the alignment notches 110 can be formed of a separate component, such as the support ledge 100 or the upturned hook 104, for example but without limitation.

In the illustrated configuration, the upturned hook 104 can help resist twisting of the printed circuit board 92 when the tail 70 is pulled into position such that wires of the tail 70 are secured within the attachment notches 108 and the alignment notches 110. In addition, the buttresses 102 can help reduce the likelihood of bending or warping of the printed circuit board 92 during soldering of wires of the tail 70 to the solder pads 106.

Figure 9:
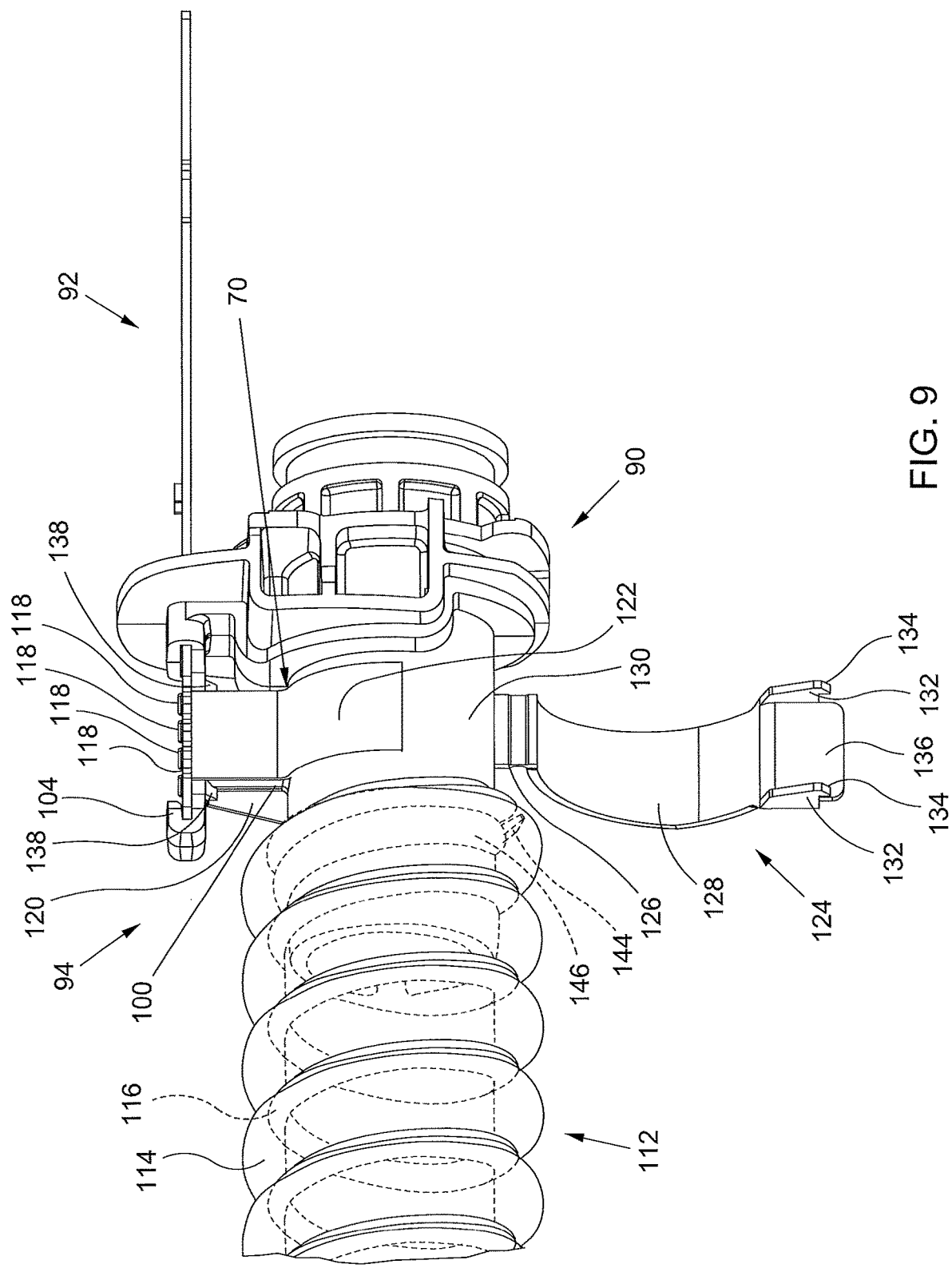

With reference now to FIG. 9, the plug portion 90 is shown with a conduit 112 attached. The conduit 112 can have any suitable configuration, including any configuration described elsewhere herein. The illustrated conduit 112 comprises a first element 114 and a second element 116. In some configurations, the first element 114 may terminate before the second element 116, with the tail 70 extending from the second element 116. In other words, the tail 70 of the second element 116 may extend further along the plug portion 90 than the first element 114. In some configurations, the tail 70 may extend from the first element 114. In some configurations, the tail 70 may extend from a combination of the first element 114 and the second element 116. In some configurations, the first element 114 and the second element 116 are helically wound at a certain pitch.

The second element 116 can comprise a bead that incorporates one or more wires 118. The wires 118 can have any suitable configuration. In some configurations, the wires 118 can be coated to have two or more colors. In other words, in some configurations, the wires 118 can be variantly coated or otherwise colored such that some of the wires 118, e.g., the outermost of the wires 118, can be visually distinguished from other of the wires 118, e.g., the innermost of the wires 118. Such a configuration, or another configuration that allows visual distinction between or among the wires 118, advantageously allows verification that the wires 118 are in a desired location and order in the respective attachment notches 108 prior to being soldered to the solder pads 106 of the printed circuit board 92.

In some configurations, the tail 70 can comprise a first flattened region 120 and a second flattened region 122, and the wires 118 can be exposed between the first flattened region 120 and the second flattened region 122. The tail 70, thus, can have any suitable configuration, including any of those described herein. In some configurations, the second flattened region 122 can be omitted. In some configurations, the first flattened region 120 and the second flattened region 122 can be omitted. The first flattened region 120 and the second flattened region 122, however, help to reduce the likelihood of contact between the wires 118 during or following manufacture. In some configurations, the tail 70 can comprise a transition or preliminary portion, between the first element 114 and/or the second element 116 and the first flattened region 120, that is not flattened or is less flattened than the first flattened region 120.

With reference to FIGS. 8 and 9, the second flattened region 122 can be restrained in position during manufacture using a cover 124. The cover 124 can be integrally formed with the plug portion 90. The cover 124 can be formed separate of the plug portion 90. The separately formed cover 124 can be secured to the plug portion 90 in any suitable configuration. In the illustrated configuration, a living hinge 126 can be used to secure the integrally formed cover 124 to the plug portion 90. Other suitable configurations also can be used.

As illustrated in FIG. 9, the cover 124 can comprise a curved inner surface 128. The curved inner surface 128 can be used to secure at least a portion of the second flattened region 122 against an outer surface 130 of the plug portion 90. In some configurations, a least a portion of the second flattened region 122 can be secured between the outer surface 130 of the plug portion 90 and the curved inner surface 128 of the cover 124. In some configurations, at least a portion of the first flattened region 120 can be secured between the outer surface 130 of the plug portion 90 and the inner surface 128 of the cover 124. In some configurations, at least a portion of the wires 118 exposed between the first flattened region 120 and the second flattened region 122 can be secured between the outer surface 130 of the plug portion 90 and the inner surface 128 of the cover 124.

The cover 124 can comprise one or more retention members 132. In the illustrated configuration, two retention members 132 are provided. Each of the retention members 132 can comprise a hook member 134. The two retention members 132 can be separated from each other by a tab 136. The tab 136 can provide a surface for the operator to press to close the cover 124 against the plug portion 90. The tab 136 can also cover at least a part of the second flattened region 120 when the cover 124 is closed against the plug portion 90. Other configurations can be used that do not comprise the tab 136, keeping in mind the desire to provide for ease of assembly and coverage of the second flattened region 120. The plug portion 90 can comprise one or more catches 138. The catches 138 can be positioned on the support ledge 100. The catches 138 can be positioned on a lower surface of the support ledge 100. Other configurations are possible keeping in mind a desire to secure the cover 124 in a closed position that captures the second flattened region 122. During assembly, with the second flattened region 122 positioned along the outer surface 130 of the plug portion 90, the cover 124 can be rotated about the living hinge 126 until the retention members 132 engage with the catches 138, which traps the second flattened region 122 between the outer surface 130 and the curved inner surface 128 of the cover 124.

In some configurations, the connection between the conduit 112 and the plug portion 90 and/or the connection between the wires 118 and the printed circuit board 92 can be overmolded. In some configurations, the cover 124 can be overmolded. In some configurations, the connection between the conduit 112 and the plug portion 90, as well as the connection between the wires 118 and the printed circuit board 92, and the cover 124 can be overmolded.

Figure 10:
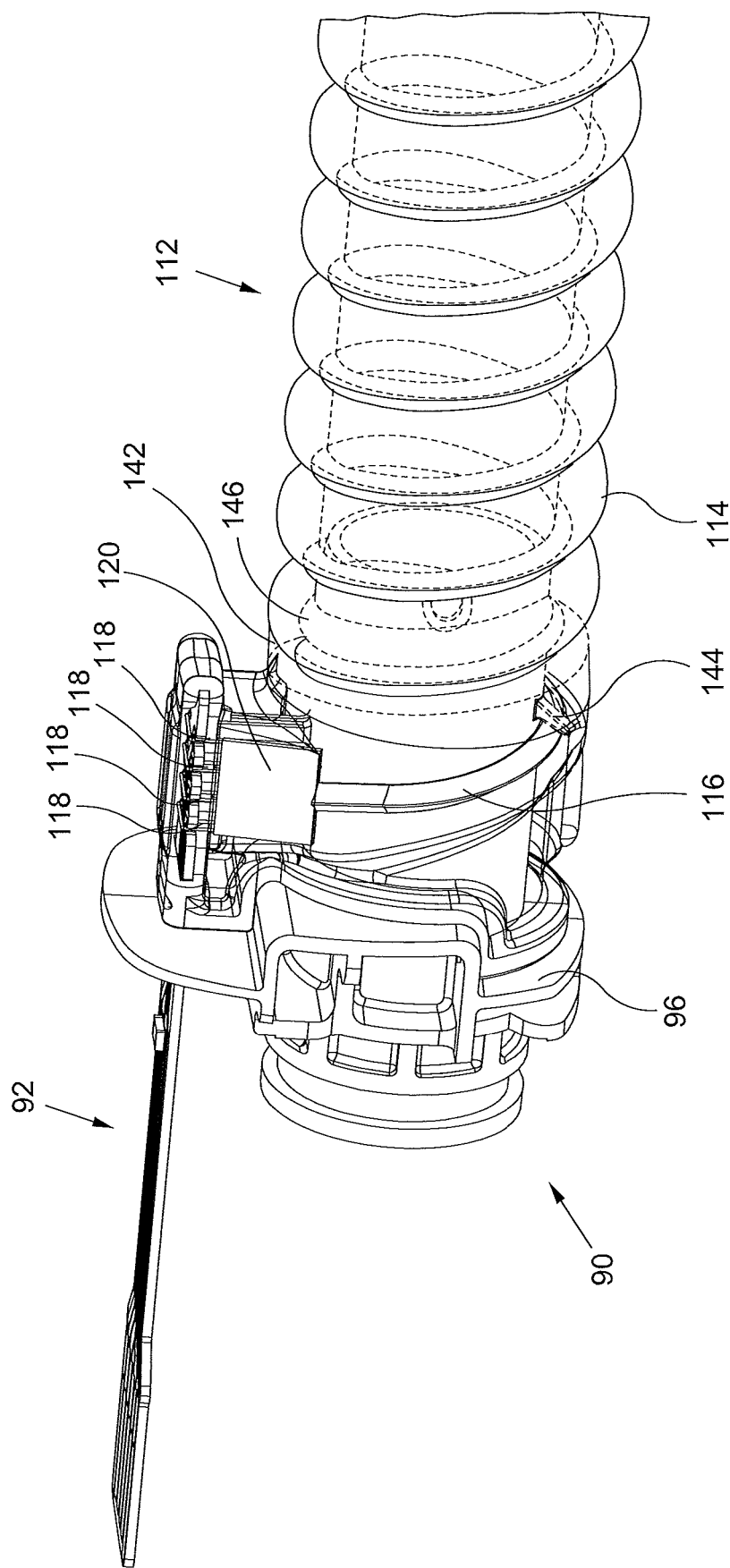

In some configurations, as shown in FIG. 10, a flow of an overmold material 142 can be limited during overmolding. The overmold material 142 can be any suitable material. In some configurations, the overmold material 142 can be any material suitable for use in lower pressure overmolding. In some configurations, the overmold material 142 can be a thermoplastic elastomer (TPE), such as a thermoplastic polyurethane (TPU), a thermoplastic vulcanizate (TPV), or a polyolefin elastomer (POE), similar to or the same as the material used to form the tube 6. In some configurations, the overmold material 142 can be a thermoplastic polymer such as a low-density polyethylene (LDPE) or a polypropylene (PP). In some configurations, where the plug portion 90 is a polypropylene, the tube 6 (including the tails 70, 72) is a polyolefin elastomer, and the printed circuit board 92 is a glass-reinforced epoxy laminate, the overmold material 142 can be an ethylene copolymer with a methylacrylate component, which bonds to the plug portion 90, the tails 70, 72, and the printed circuit board 92 and thereby provides pneumatic leak protection and liquid ingress protection. In some configurations, the printed circuit board 92 may be insert-molded as part of, or otherwise bonded to, the plug portion 90, and the overmold material 142 can be a thermoplastic elastomer selected to bond to the plug portion 90 and the tails 70, 72.

In some configurations, the overmold material 142 can flow into at least a portion of the first element 114. In other words, the first element 114 can be an elongate hollow element and the overmold material 142 can flow into at least a portion of the elongate hollow element to help reduce the likelihood of leaks. In some configurations, the overmold material 142 can at least partially melt the second element 116. By at least partially melting the second element 116, the overmold material 142 and the second element 116 can help to reduce the likelihood of leaks. In some configurations, the overmold material 142 can provide protection to the electrical components (e.g., can effectively pot the electrical components).

As illustrated in FIGS. 8-10, the plug portion 90 can comprise a guidance tab 144. The guidance tab 144 can be integrally formed with the plug portion 90. The guidance tab 144 can act as a positive stop for the conduit 112 during assembly of the conduit 112 onto the plug portion 90. In the illustrated configuration, the plug portion 90 comprises a helical rib 146. In some configurations, the helical rib 146 can align with the pitch of the conduit 112. The plug portion 90 can be inserted into the conduit 112 until the guidance tab 144 is positioned between the tail 70 and the conduit 112. The helical rib 146 can then help to hold the conduit 112 in place on the plug portion 90 by pressing into the first element 114. In some configurations, the guidance tab 144 is bent toward the mounting flange 96. which can help direct the tail 70 towards the printed circuit board 92. Because the length of the tail 70 and the length of the first flattened region 120 are known, it is possible to provide a desired length between the end of the first element 114 and the point of connection of the exposed wires 118 to the solder pads 106 of the printed circuit board 92. Other configurations are possible keeping in mind a desire to properly locate the terminal end of the conduit 112 relative to the printed circuit board 92.

Figure 10A:
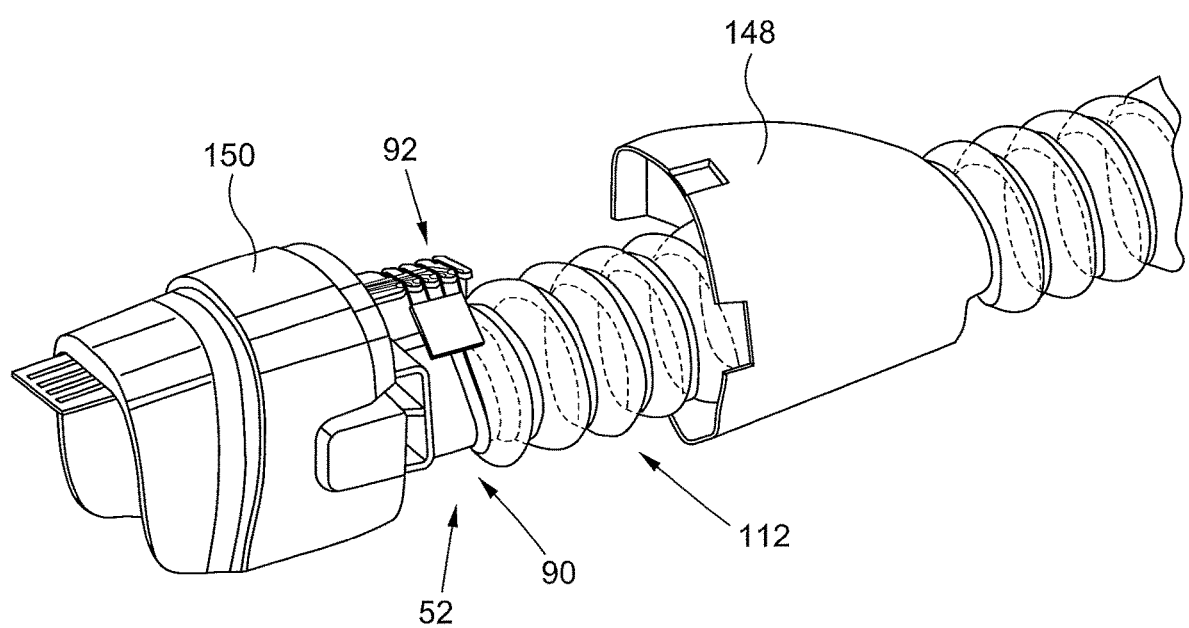

With reference to FIG. 10A, the assembly discussed above—including but not limited to portions of the chamber-end connector 52, portions of the conduit 112, and/or portions of the printed circuit board 92—can be encapsulated by a first outer cover 148 and a second outer cover 150. The two outer covers 148, 150 can be secured in any suitable manner. In the illustrated configuration, the two outer covers 148, 150 can be snap-fit to the mounting flange 96 of the plug portion 90. Other configurations are possible.

Figure 11A:
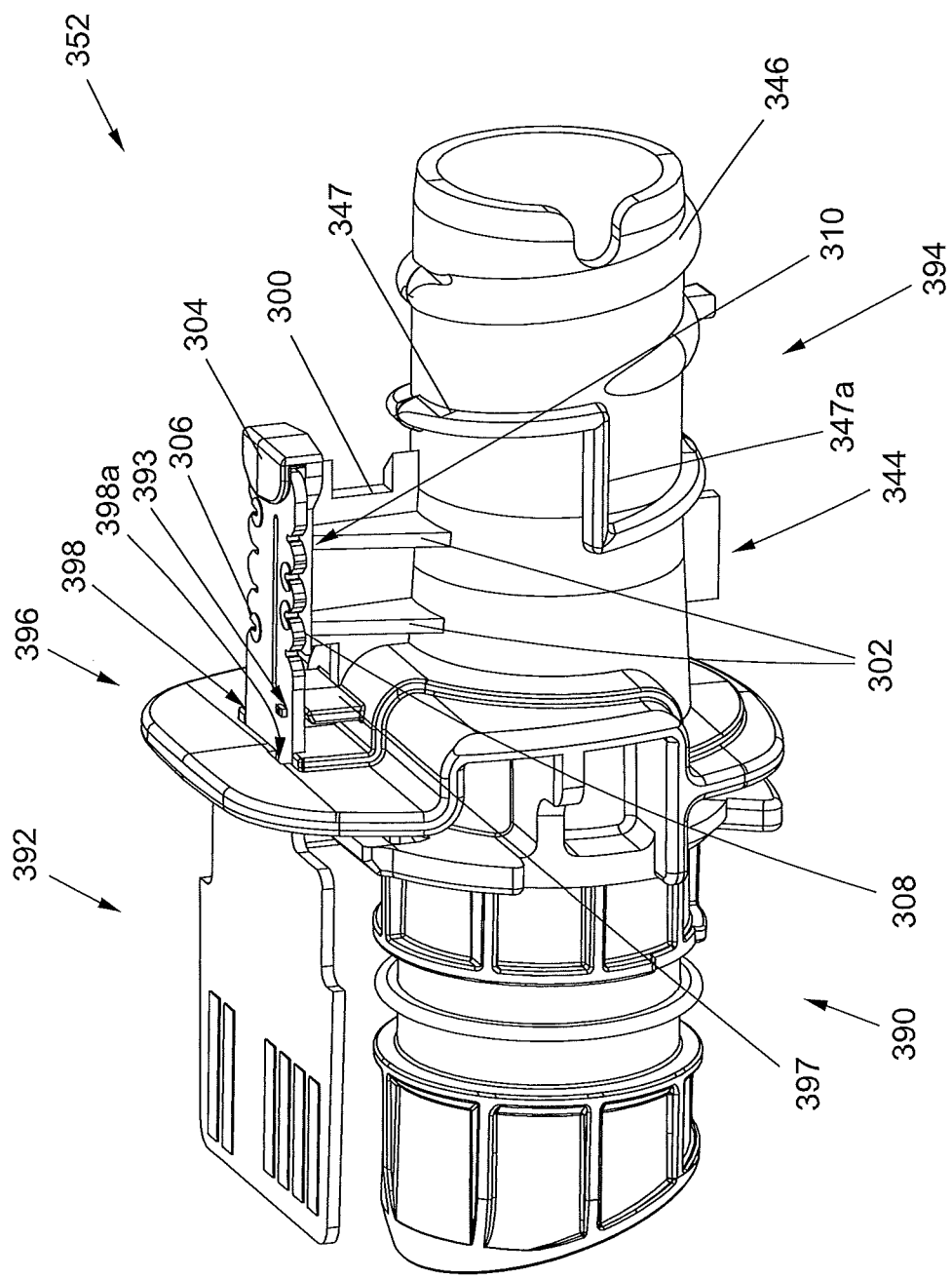
FIGS. 11A-11C are views of another example embodiment of a chamber-end connector.
Figure 11B:
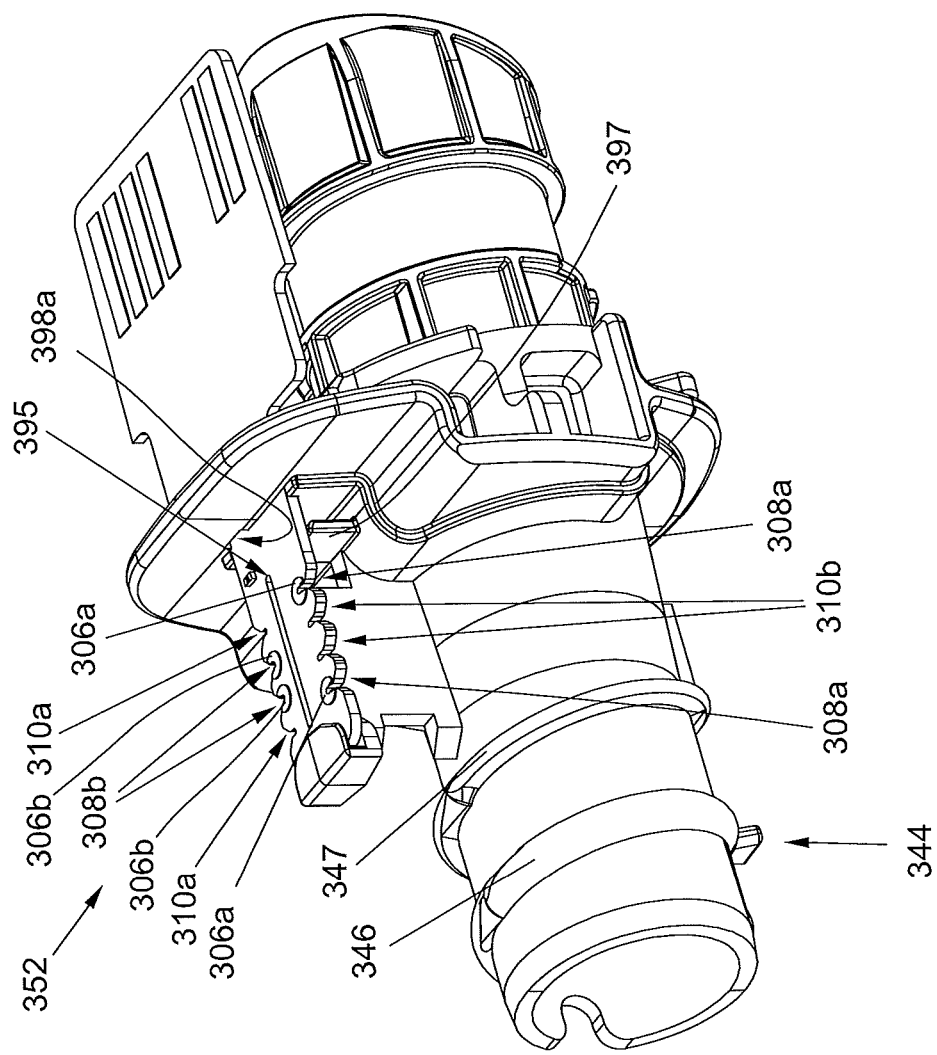
Figure 11C:
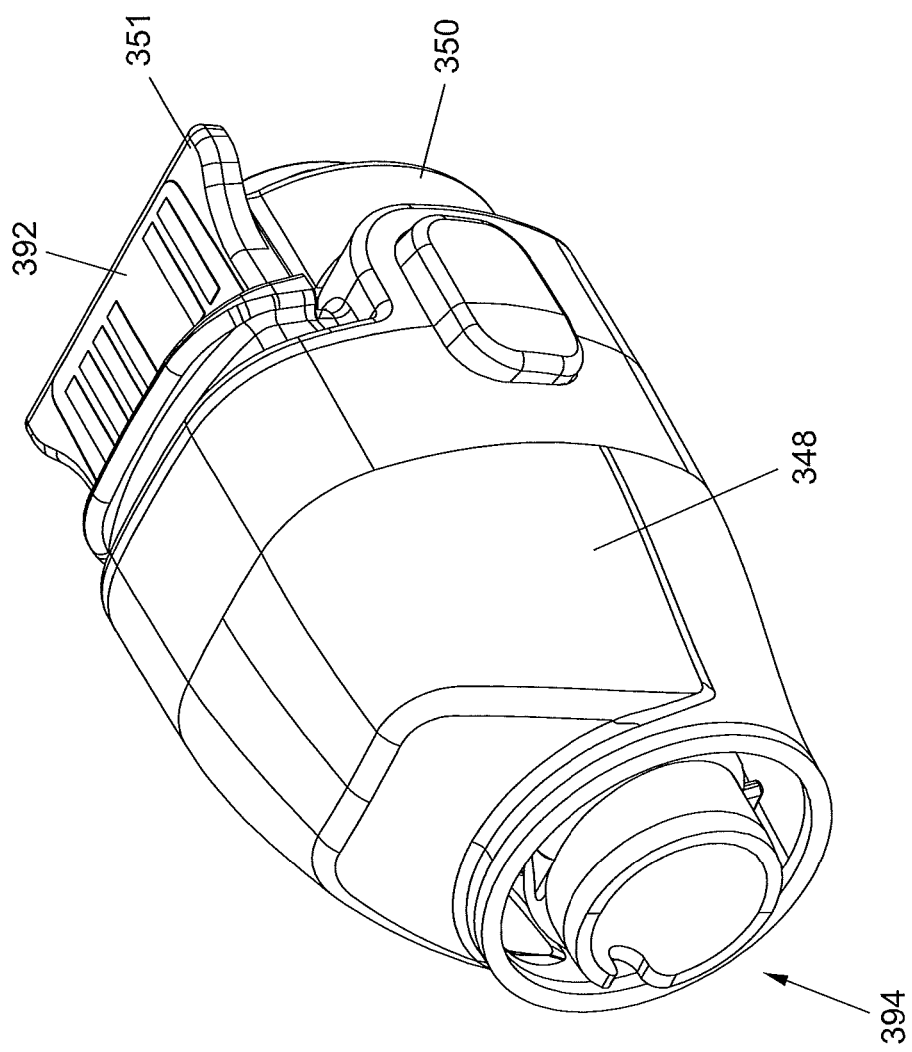

FIGS. 11A-11C illustrate another example embodiment of a chamber-end connector 352. FIGS. 11A-11B illustrate the chamber-end connector 352 without an outer cover or housing, and FIG. 11C illustrates the chamber-end connector 352 encapsulated by a first outer cover 348 and a second outer cover 350 that are secured to each other and/or underlying components of the connector 352.

The chamber-end connector 352 comprises a plug portion 390 that can support a printed circuit board or PCB 392. The plug portion 390 comprises a main body 394 that can be generally cylindrical. A mounting flange 396 can extend away from the main body 394. The mounting flange 396 defines a passage 398 through which the PCB 392 can extend. The mounting flange 396 also defines an extension 398a of the passage 398 extending from the passage 398, and extending from the PCB 392 when the PCB 392 extends through the passage 398. In the embodiment shown in FIG. 8, an electronic component 93, such as but not limited to an ID resistor, is positioned on the PCB 92 on the chamber side of the mounting flange 96, i.e., on the opposite side of the mounting flange 96 from the alignment notches 110. In the embodiment of FIGS. 11A-11C, an electronic component 393, such as but not limited to an ID resistor, is positioned on the PCB 392 on the conduit side of the mounting flange 396, i.e., on the same side of the mounting flange 396 as alignment notches 310. Placement of the electronic component 393 on the conduit side of the mounting flange 396 allows the electronic component 393 to be covered by the overmold material as described herein to advantageously help protect the electronic component 393 from liquid. The extension 398a of the passage 398 provides an opening for the electronic component 393 to pass through the mounting flange 396 during assembly.

A support ledge 300 can be formed adjacent to the passage 398. The support ledge 300 is arranged and configured to underlie and support the PCB 392. In the illustrated embodiment, the support ledge 300 has a height that is 0.02 to 0.1 mm higher, i.e., farther from the central axis of the plug portion 390, than the bottom of the passage 398. This increased height causes the portion of the PCB 392 on the conduit side of the mounting flange 396 to bend or lift slightly upwards, i.e., away from the central axis of the plug portion 390. This then causes the portion of the PCB 392 on the chamber side of the mounting flange 396 to be deflected or bent slightly downward, i.e., closer to the central axis of the plug portion 390, which forces the chamber end of the PCB 392, i.e., the end of the PCB 392 on the chamber side of the mounting flange 396, more tightly into contact with the underlying surface of the chamber-end connector 352. As shown in FIG. 11C, the second outer cover 350 configured to enclose portions of the plug portion 390 and the PCB 392 comprises a ledge 351. The ledge 351 is configured to underlie and support the chamber end of the PCB 392. The height of the support ledge 300 pressing upward on the portion of the PCB 392 on the conduit side of the mounting flange 396 drives the portion of the PCB 392 on the chamber side of the mounting flange 396 downwards, which helps promote the chamber end of the PCB 392 lying flush with, or slightly below the upper surface of, the ledge 351. This helps inhibit the PCB 392 from potentially being snagged on surrounding objects and reduces the likelihood of separation between the PCB 392 and the ledge 351. In some configurations the ledge 351 can contain a recess that receives at least a portion of the PCB 392. In the illustrated embodiment, the support ledge 300 is reinforced by two buttresses 302. The support ledge 300 can comprise an upturned hook 304 to overlie a portion of the PCB 392.

As illustrated, the PCB 392 comprises one or more attachment notches 308, solder pads 306 that at least partially surround the attachment notches 308, and alignment notches 310. In this embodiment (and as best shown in FIG. 11B), the PCB 392 comprises four attachment notches 308 at least partially surrounded by four solder pads 306 and four corresponding alignment notches 310. The outermost two attachment notches 308a and solder pads 306a are positioned on a first edge of the PCB 392, and the corresponding outermost two alignment notches 310a are positioned on the second, opposing edge of the PCB 392 in alignment with the attachment notches 308a. The inner two attachment notches 308b and solder pads 306b are positioned on the second edge of the PCB 392 between the outer alignment notches 310a, and the inner two alignment notches 310b are positioned on the first edge of the PCB 392 between the attachment notches 308a and in alignment with the attachment notches 308b.

In some embodiments, the outer solder pads 306*a* are configured to be soldered to the heater wires 14, and the inner solder pads 306*b* are configured to be soldered to the sensing wires 18. Soldering the heater wires 14 to the outer solder pads 306*a* and on the opposite edge of the PCB 392 from the sensing wire solder pads 306*b* advantageously increases the separation between the heater wire solder pads 306*a* and the sensing wire solder pads 306*b*. This helps inhibit or reduce the likelihood of liquid bridging between the heater wire solder pads 306*a* and the sensing wire solder pads 306*b* and thus shorting the heater wires 14 to the sensing wires 18. In the illustrated embodiment, the PCB 392 also comprises a slot 395. As shown, the slot 395 extends lengthwise along a portion of the PCB 392 on the conduit side of the PCB 392. The slot 395 is positioned between the outer solder pads 306*a* and the inner solder pads 306*b*. During the overmolding process as described herein, overmold material flows into the slot 395, which also helps to separate the heater wire solder pads 306*a* from the sensing wire solder pads 306*b* and helps to inhibit liquid from bridging between them. The separation between the heater wire solder pads 306*a* and the sensing wire solder pads 306*b* also helps to reduce the likelihood of heat transfer between the heater wires and the sensing wires.

The chamber-end connector 352 of FIGS. 11A-11C can also comprise a cover (not shown) configured to restrain the second flattened region 122 during manufacture. The cover can be similar to the cover 124 shown in FIGS. 8 and 9. However, the cover for the embodiment shown in FIGS. 11A-11C may only comprise one retention member 132. In other words, the cover may attach to only one end of the support ledge 300 rather than attaching to two ends of the support ledge 300.

In some embodiments, portions of and/or connections among the plug portion 390, the wires 118, the conduit 112, and the PCB 392 can be overmolded similar to the embodiment of FIGS. 8-10A. As described above, in the embodiment of FIGS. 11A-11C, the electronic component 393 can also be overmolded due to the placement of the electronic component 393 on the conduit side of the PCB 392. The plug portion 390 can comprise a partitioning wall 397 as shown in FIGS. 11A-11B. The partitioning wall 397 divides the space below the PCB 392 between the mounting flange 396 and the buttresses 302 of the support ledge 300. The division of this space into two smaller spaces by the partitioning wall 397 advantageously helps reduce the likelihood of the overmold material forming voids or shrinking excessively as it cools.

The plug portion 390 can comprise a guidance tab 344 that can act as a positive stop for the conduit 112 during assembly of the conduit 112 onto the plug portion 390. In the illustrated embodiment, the guidance tab 344 protrudes from the plug portion 390 normal to the plug portion 390 wall rather than at an angle as in the embodiment of FIGS. 8-10A. The plug portion 390 comprises two helical ribs 346, 347. In some embodiments, the first helical rib 346 and/or the second helical rib 347 can align with the pitch of the conduit 112. In the illustrated embodiment, the second helical rib 347 has a roughly trapezoidal cross section that creates a sharp transition or change in slope from the outer surface of the plug portion 390 to the outer surface of the second helical rib 347, whereas the first helical rib 346 has a roughly semicircular cross section that creates a smoother transition. The sharp angles of the second helical rib 347 can help prevent or reduce the likelihood of liquid passing over the second helical rib 347. The plug portion 390 can be inserted into the conduit 112 until the guidance tab 344 is positioned against a cut portion of the first element 114. The first helical rib 346 can then help to hold the conduit 112 on the plug portion 90 by pressing into the first element 114. As shown, the guidance tab 344 can extend from the first helical rib 346. The second helical rib 347 is positioned between the first helical rib 346 and the support ledge 300. As shown in FIG. 11A, the second helical rib 347 comprises a longitudinal bridging segment 347*a* such that the second helical rib 347 fully encircles the plug portion 390. The second helical rib 347 can act as a liquid barrier to inhibit liquid from transferring from the conduit 112 toward the PCB 392.

Figure 12:
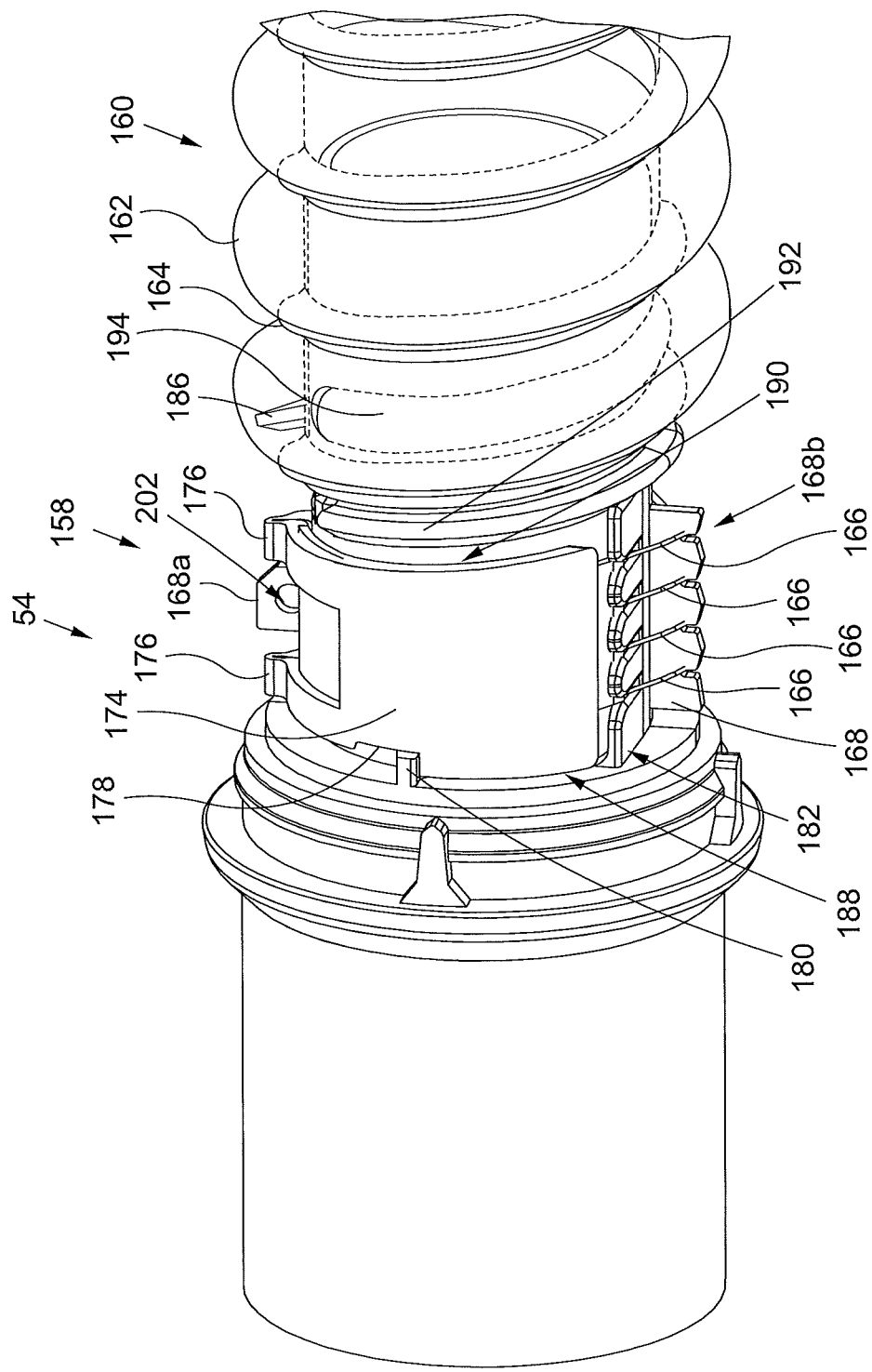
FIG. 12 is a perspective view of a portion of a patient-end connector.

With reference now to FIG. 12, the patient-end connector 54 is shown coupled to an end of a conduit 160. The patient-end connector 54 can comprise a single integrally formed main body 158. Other configurations also are possible.

As described above, the conduit 160 can have any suitable configuration, including any configuration described elsewhere herein. The illustrated conduit 160 comprises a first element 162 and a second element 164. The first element 162 may terminate before the second element 164, with the tail 82 (not visible in FIG. 12) extending from the second element 164. In other words, the tail 82 of the second element 164 may extend further along the main body 158 of the patient-end connector 54 than the first element 162. In some configurations, the tail 82 may extend from the first element 162. In some configurations, the tail 82 may extend from a combination of the first element 162 and the second element 164. In some configurations, the first element 162 and the second element 164 are helically wound with a certain pitch.

The second element 164 can comprise a bead that incorporates one or more wires 166. The wires 166 can have any suitable configuration. In some configurations, the wires 166 can be coated to have two or more colors. In other words, in some configurations, the wires 166 can be variantly coated or otherwise colored such that some of the wires 166, e.g., the outermost of the wires 166, can be visually distinguished from other of the wires 166, e.g., the innermost of the wires 166. Such a configuration, or another configuration that allows visual distinction between or among the wires 166, advantageously allows verification that the wires 166 are in a desired location and order for connection to a printed circuit board 168.

In some configurations, the tail 82 can comprise a first flattened region 170 and a second flattened region 172 (not visible in FIG. 12), and the wires 166 can be exposed between the first flattened region 170 and the second flattened region 172. The tail 82, thus, can have any suitable configuration, including any of those described elsewhere herein. In some configurations, the second flattened region 172 can be omitted. In some configurations, the first flattened region 170 and the second flattened region 172 can be omitted. The first flattened region 170 and the second flattened region 172, however, help to reduce the likelihood of contact between the wires 166 during or following manufacture. In some configurations, the tail 82 can comprise a transition or preliminary portion, between the first element 162 and/or the second element 164 and the first flattened region 170, that is not flattened or is less flattened than the first flattened region 170.

With continued reference to FIG. 12, in some embodiments the second flattened region 172 can be restrained in position during manufacture using a cover 174. The cover 174 can be integrally formed with the main body 158. The cover 174 can be formed separate of the main body 158. The separately formed cover 174 can be secured to the main body 158 in any suitable configuration. In the illustrated configuration, a living hinge 176 can be used to secure the integrally-formed cover 174 to the plug portion 90. In the illustrated configuration, two separate living hinges 176 have been used. Other suitable configurations also can be used. In some embodiments, the second flattened region 172 can be cut off after the exposed wires 118 have been soldered to the solder pads 106, and no cover is used.

In the illustrated configuration, the cover 174 comprises a first edge 188 and a second edge 190 and comprises a recess 178 that can be positioned along the first edge 188. A post 180 of the main body 158 can be used to secure the cover 174 in a closed position. The post 180 and the recess 178 can interact to secure the cover 174 in the closed position. A spine 192 can align with the pitch of the conduit 160. In some configurations, the second edge 190 can align with the pitch of (or extend generally parallel to) the spine 192. The second edge 190 and the spine 192, when thus aligned, can interact to help secure the cover 174 in the closed position by preventing movement of the recess 178 away from the post 180. As discussed above, the cover 174 can secure the second flattened region 172 and/or the wires 166 in position between the main body 158 and the cover 174.

With reference to FIG. 12, the main body 158 can comprise a wire alignment component, such as a comb 182, for example but without limitation. The comb 182 can comprise a plurality of fingers spaced by gaps or alignment notches that receive the wires 166. The comb 182 can help to reduce or eliminate the likelihood of the wires 166 crossing each other and can help to maintain the wires 166 taut during soldering to the printed circuit board 168. In the illustrated configuration of FIG. 12, the comb 182 extends generally normal to the printed circuit board 168.

Figure 13:
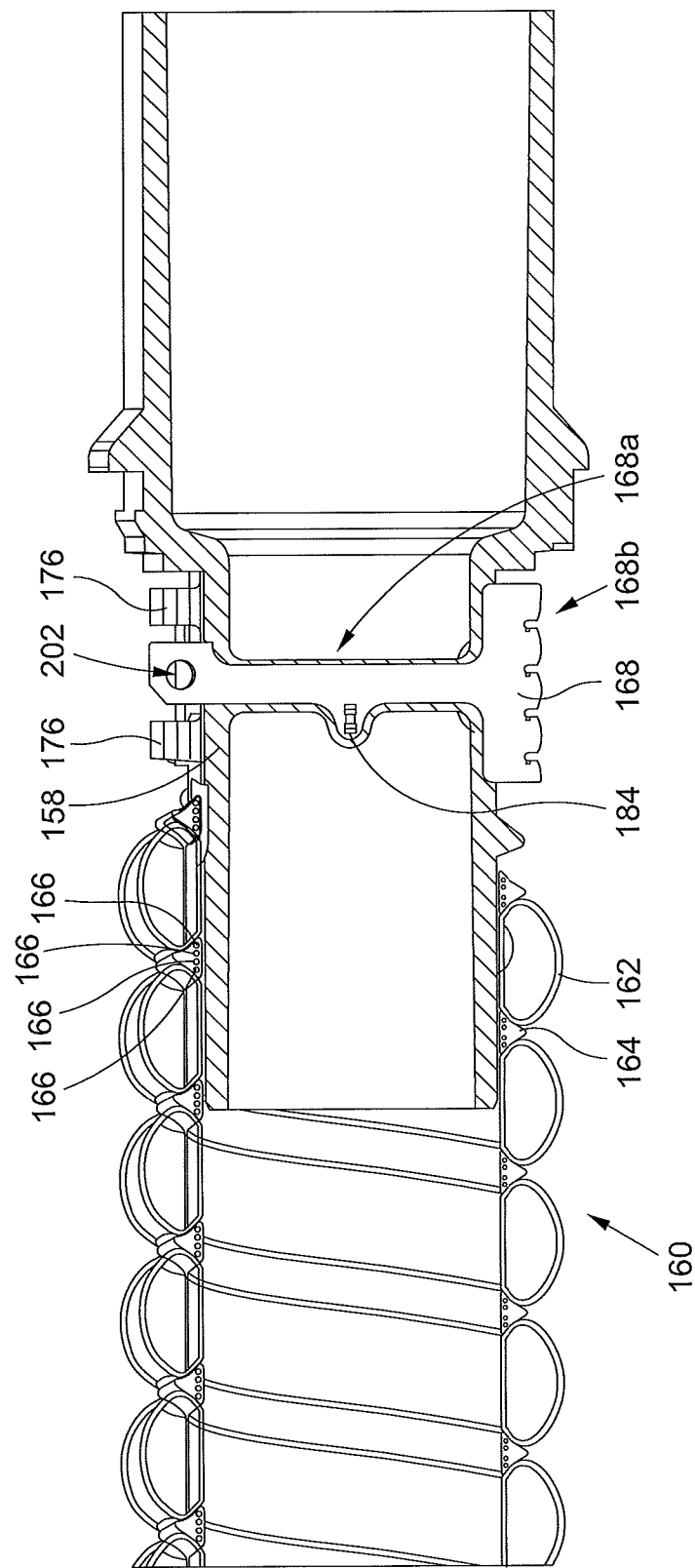
FIG. 13 is a cross section of a portion of a patient-end connector.

As illustrated in FIG. 13, the printed circuit board 168 preferably extends fully through the diameter of the main body 158. In other words, at least a portion of the printed circuit board 168 can be exposed beyond the main body 158 at either or both ends of the printed circuit board 168. As illustrated in FIG. 13, the printed circuit board 168 has a wider head part 168*b* and a narrower stem part 168*a* that extends through the gases flow path of the main body 158. At least a portion of the head part 168*b* preferably extends beyond the main body 158. In some embodiments, as illustrated in FIG. 13, at least a portion of the stem part 168*a* extends beyond the main body 158. In some embodiments, at least a portion of the stem part 168*a* extends into a thickness of the main body 158 but not beyond the main body 158. The stem part 168*a* joins to the head part 168*b* within a thickness of the main body 158. In other words, at least a portion of the head part 168*b* is embedded within the wall of the main body 158, as shown in FIG. 13. The head part 168*b* comprises the solder pads 106, and embedding a portion of the head part 168*b* into the wall of the main body 158 helps the printed circuit board 168 to resist flexure during assembly.

With continued reference to FIG. 13, the printed circuit board 168 is shown with a thermistor 184 attached to the printed circuit board 168. The thermistor 184 can be a surface mount thermistor. Other sensors can be mounted to the printed circuit board 168. In some embodiments, the thermistor 184 is used to sense temperature and to feed a value representing the temperature back to the printed circuit board 168 and from the printed circuit board 168 to a further medical device.

The thermistor 184 as well as the printed circuit board 168 can be overmolded during formation of the patient-end connector 54. Because of the clamping and material flow pressures that occur during the overmolding process, the orientation of the components and the bending or flexure of the printed circuit board 168 become important considerations. For this reason, the thermistor 184 is mounted lengthwise in the direction of gases flow through the patient-end connector 54. The lengthwise mounting in the direction of gases flow reduces the impact of possible flexure of the printed circuit board 168 during the overmolding operation. In other words, the thermistor 184 preferably is mounted with the terminals oriented relative to each other in a direction that has the least amount of flexure of the printed circuit board 168.

The thermistor 184 can be positioned on an extended portion of the printed circuit board 168 that extends further upstream into the gases flow relative to other portions of the printed circuit board 168 and the mounting of the printed circuit board 168 to the main body 158. By positioning the thermistor 184 on this extended portion of the printed circuit board 168, the thermistor 184 will be positioned in a more laminar gases flow, before the turbulence in the gases flow that can be created by the other portions of the printed circuit board 168 and the mounting of the printed circuit board 168 to the main body 158. In addition, it is believed that positioning the thermistor 184 on the extended portion of the printed circuit board 168 can help to reduce the impact of stem effects on the readings from the thermistor 184 that can be caused by temperature variations generated by other electronic components on the printed circuit board 168 and/or ambient conditions.

With continued reference to FIG. 12, the main body 158 can comprise a guidance tab 186. The guidance tab 186 can be integrally formed with the main body 158. The guidance tab 186 can act as a positive stop during assembly of the conduit 160 onto the main body 158. In the illustrated configuration, the main body 158 comprises a helical rib 194 The helical rib 194 can match or simulate the pitch of the conduit 160. Thus, the conduit 160 can be threaded onto the main body 158 (or the main body 158 can be threaded into the conduit 160) until the first element 162 (e.g., the elongate hollow portion of the conduit 160) bumps against the guidance tab 186. In some embodiments, the guidance tab 186 may be bent away from the body of the conduit 160, which can help direct the tail 82 towards the printed circuit board 168. In some embodiments, the guidance tab 186 protrudes normal to the main body 158. Because the length of the tail 82 and the length of the first flattened region 170 are known, it is possible to provide a desired length between the end of the first element 162 and the connection of the exposed wires 166 to the solder pads 106 of the printed circuit board 168. Other configurations are possible keeping in mind a desire to properly locate the terminal end of the conduit 160 relative to the printed circuit board 168.

Figure 13A:
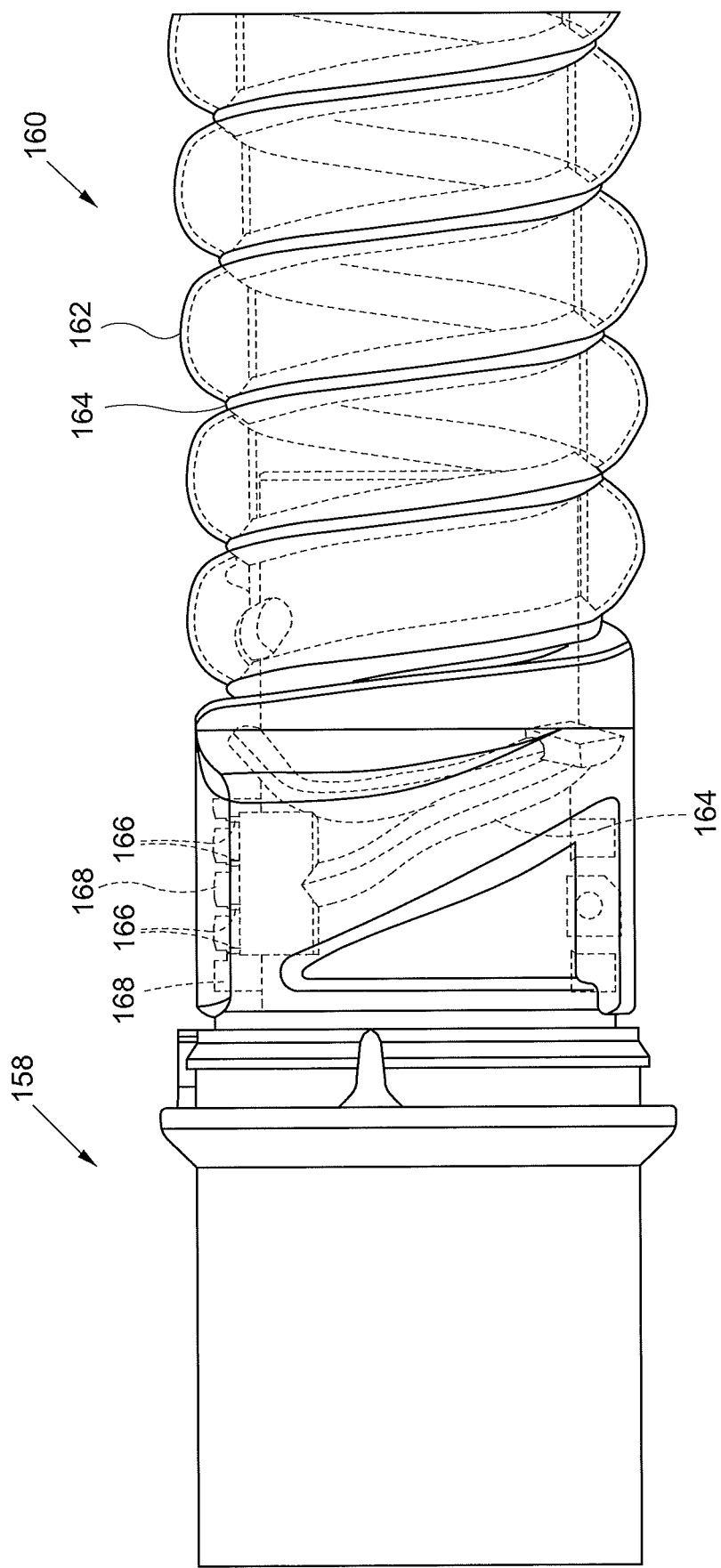
FIG. 13A is a side view of a portion of a patient-end connector.

As with the chamber-end connector 52 described above, the connection between the conduit 160 and the main body 158 and/or the connection between the printed circuit board 168 and the wires 166 can be overmolded. With reference to FIG. 13A, an overmold material 189 is shown at the juncture between the conduit 160 and the main body 158. The overmold material 189 can envelop the printed circuit board 168 and the wires 166. The overmold material 189 can be similar to, and have similar characteristics to, the overmold material 142 described above. In addition, while not shown, a cover member can connect to the main body 158 to enshroud the connection between the conduit 160 and the main body 158.

The intermediate connector 56 also can employ similar connections to the wires 166 and the conduit 160.

In some cases, there may be a gap or space between an outer surface of the main body 158 and an inner surface of the conduit 160 at the juncture between the conduit 160 and the main body 158. If condensate forms within the conduit 160, even a small gap could allow liquid to seep between the conduit 160 and the main body 158 and reach the printed circuit board 168 and/or the exposed wires 166. To inhibit or reduce the likelihood of liquid reaching the electrical components or connections, the main body 158 can comprise features to allow the overmold material 189 to flow into any gaps to help seal the interface between the conduit 160 and the main body 158. The overmold material 189 can therefore help better protect the electrical components from condensate or other liquids. The overmold material 189 can also help create an improved pneumatic seal between the conduit 160 and the main body 158. FIGS. 15-19 illustrate example embodiments of such features.

Figure 15:
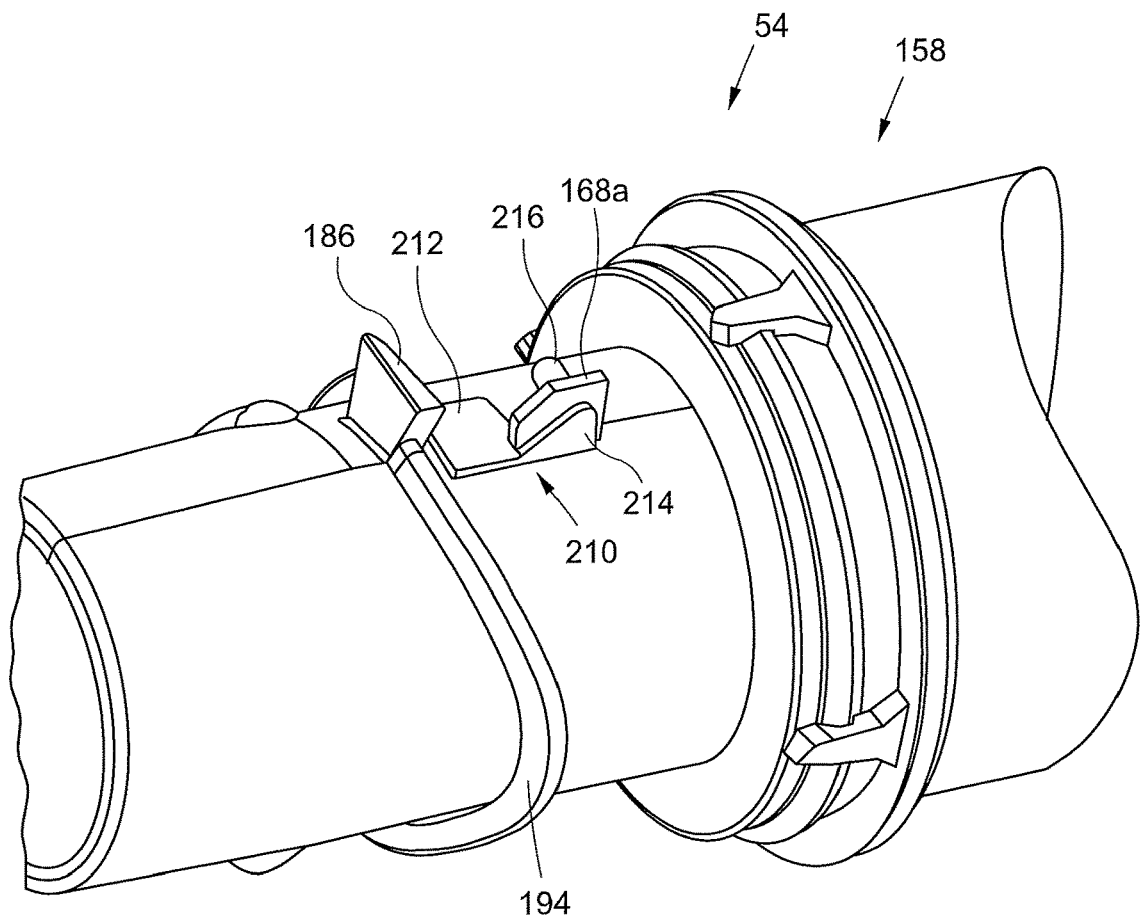
FIG. 15 is a perspective view of a portion of an embodiment of a patient-end connector including a bridge piece.

With reference to FIG. 15, in some configurations, the patient-end connector 54 comprises a bridge piece 210. The bridge piece 210 can be disposed on the outer surface of the main body 158. The bridge piece 210 can be positioned between the outer surface of the main body 158 and at least a portion of the conduit 160. In some configurations, as will be discussed, the bridge piece 210 can be positioned between the outer surface of the main body 158 and the second element 164 or bead of the conduit 160.

Figure 16:
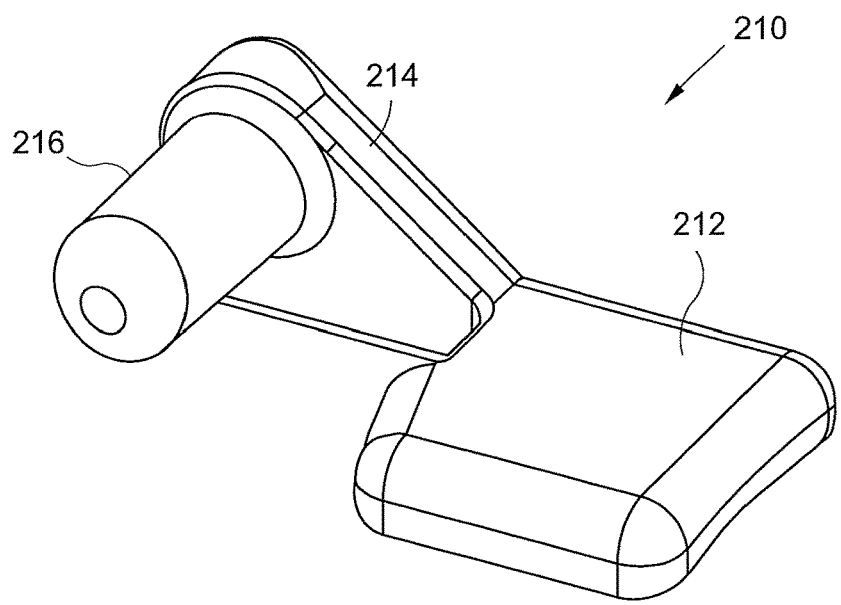
FIG. 16 is a perspective view of the bridge piece of FIG. 15.

FIG. 16 illustrates a perspective view of the bridge piece 210. As shown, the bridge piece 210 comprises a pad portion 212, an extension portion 214, and a peg 216.

The pad portion 212 can be generally square or rectangular. Other configurations also are possible. The pad portion 212 has a lower surface that is configured to contact the connector. The pad portion 212 has an upper surface that is configured to contact the conduit 160 or the second element 164 or bead of the conduit 160.

The extension portion 214 extends outward and upward from the pad portion 212. In the illustrated embodiment, the extension portion 214 is generally triangular, although other shapes or configurations are also possible. The extension portion 214 has a side surface.

The peg 216 extends from the extension portion 214. In the illustrated configuration, the peg 216 extends from the side surface of the extension portion 214.

As shown in FIGS. 12 and 13, the stem part 168a of the printed circuit board 168 extending from the main body 158 comprises a hole 202. The peg 216 is configured to be received in the hole 202, as shown in FIG. 15. With the peg 216 inserted into the hole 202, the bridge piece 210 is coupled to the main body 158. In some embodiments, the stem part 168a of the printed circuit board 168 is extended or slightly widened to provide additional strength and better support to the peg 216 and the bridge piece 210.

In the embodiment illustrated in FIG. 15, the bridge piece 210 is positioned on the main body 158 proximate and proximal to the guidance tab 186. The bridge piece 210 is positioned such that the second element 164, comprising the bead, extends over the pad portion 212 when the conduit 160 is coupled to the main body 158. The pad portion 212 therefore causes the second element 164 to lift away from the outer surface of the main body 158, thereby creating a gap between the second element 164 and the outer surface of the main body 158 on either side of the pad portion 212 (i.e., in the circumferential direction of the connector). When the overmold material 189 is applied to the juncture between the conduit 160 and main body 158, the overmold material 189 can flow into the gaps created by the bridge piece 210, thereby bonding the second element 164 to the outer surface of the main body 158. Bonding the second element 164 to the outer surface of the main body 158 can inhibit or prevent liquid from seeping between the outer surface of the main body 158 and the second element 164 or bead of the conduit 160 and thus can reduce or eliminate the likelihood of liquid reaching the electrical connections.

Figure 20:
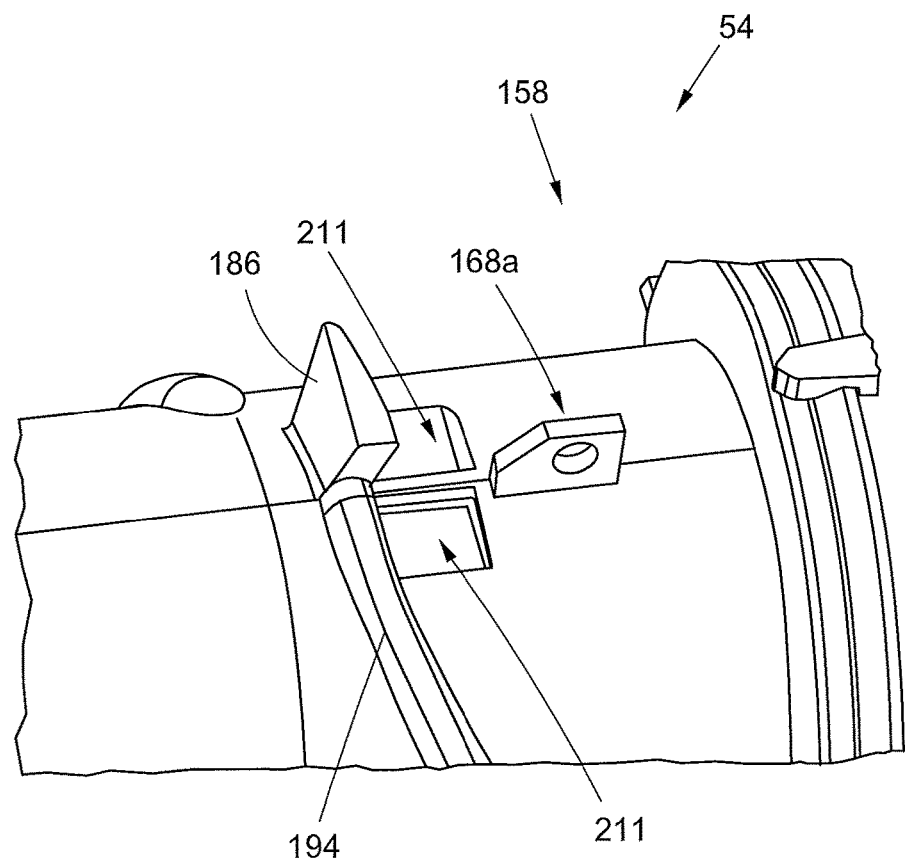
FIG. 20 illustrates a portion of an example embodiment of a patient-end connector having a bridge formed by neighboring recesses.

FIG. 20 illustrates an alternative embodiment in which a bridge member is formed on the main body 158 by two neighboring recesses 211 positioned between the stem part 168a and the tab 186. The second element 164 extends over the recesses 211, allowing overmold material to flow into the recesses 211 such that the overmold surrounds the second element 164 and bonds the second element 164 to the outer surface of the main body 158. Bonding the second element 164 to the outer surface of the main body 158 can inhibit or prevent liquid from seeping between the outer surface of the main body 158 and the second element 164 to reduce or eliminate the likelihood of liquid reaching the electrical connections.

Figure 17:
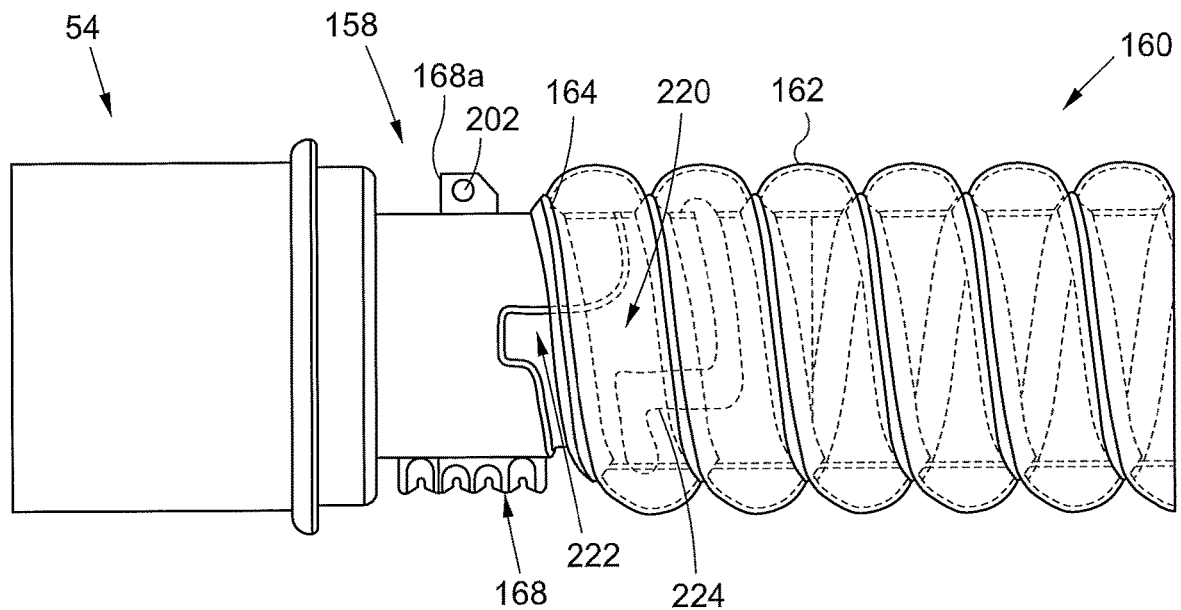
FIGS. 17-19 are various side views of a portion of a conduit coupled to an embodiment of a patient-end connector including a channel.
Figure 18:
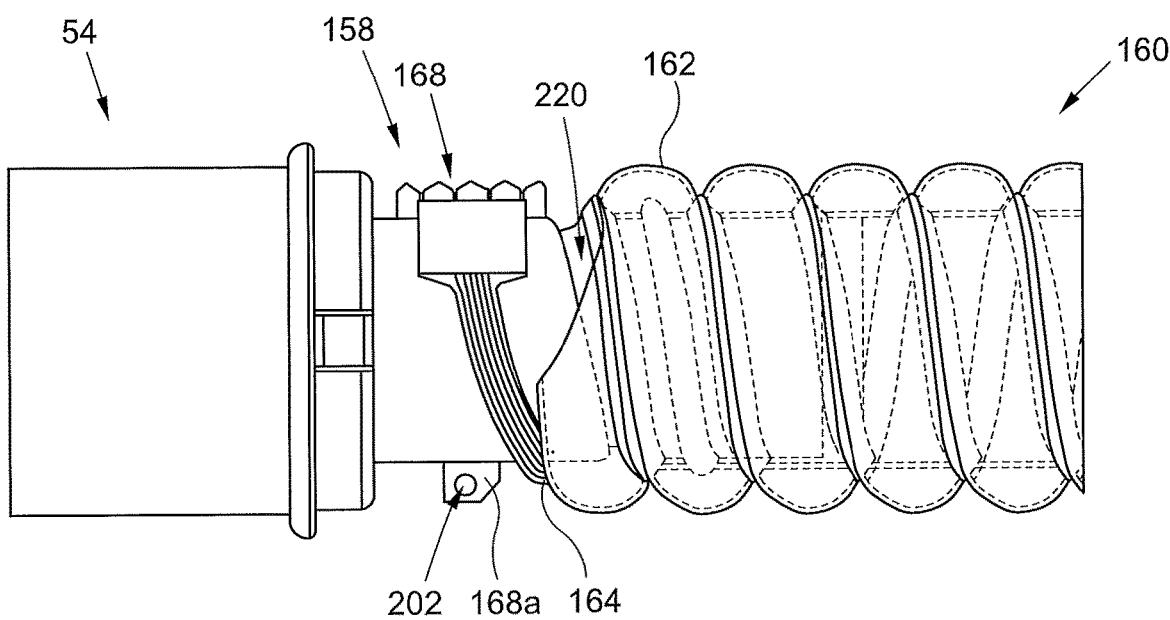
Figure 19:
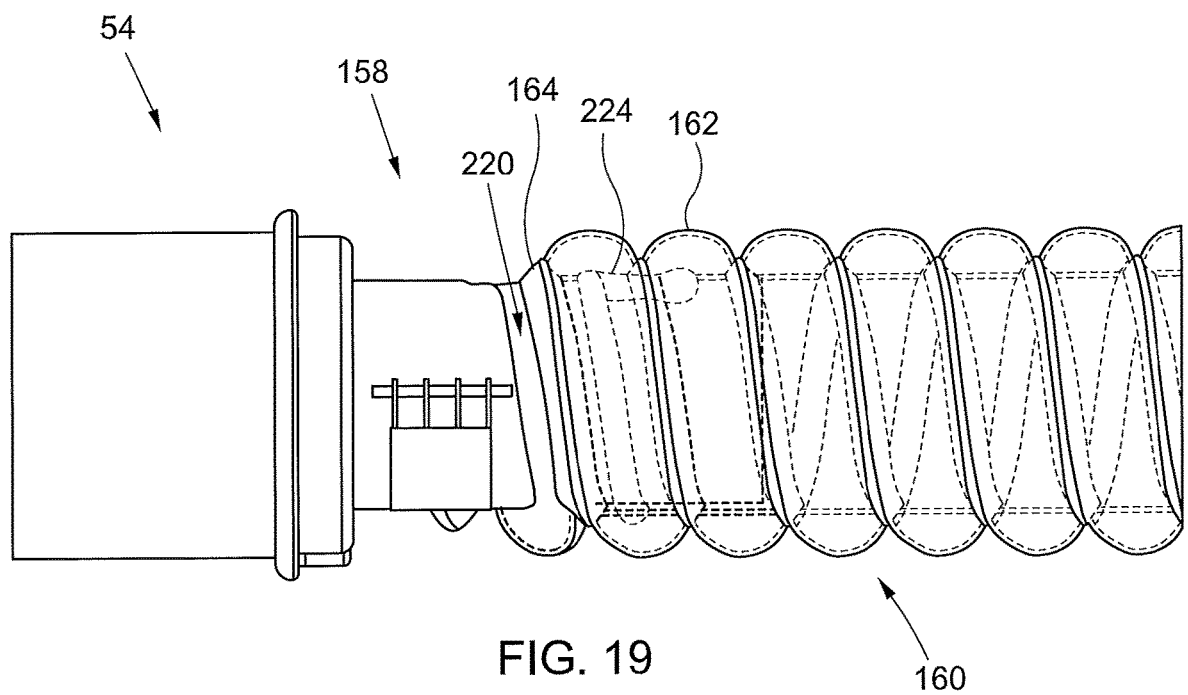

With reference to FIGS. 17-19, in some configurations, the patient-end connector 54 comprises a channel 220 formed in the main body 158. The channel 220 allows the overmold material 189 to flow between the inner surface of the conduit 160 and the outer surface of the main body 158. As shown, the channel 220 is recessed from, or formed as a recess in, the outer surface of the main body 158.

The channel 220 can have any suitable configuration. The channel 220 can extend around at least a portion of a circumference of the main body 158. In some configurations, the channel 220 can extend in a spiral or a partial spiral. The channel 220 can be positioned and formed such that the second element 164 extends over, along, or in the channel 220. When the overmold material 189 is applied to the juncture between the conduit 160 and the main body 158, the overmold material 189 can flow into the channel 220 and under the second element 164, thereby bonding the second element 164 to the outer surface of the main body 158. In some configurations, the overmold material 189 bonds the second element 164 or the conduit 160 to the recessed surface defined by the channel 220.

To aid formation of a seal between the conduit 160 and the main body 158, the channel 220 and the second element 164 can be positioned so that the channel 220 extends to both sides of the second element 164 (i.e., in an axial direction of the connector). As shown in FIG. 17, at least a portion 222 of the channel 220 is proximal of the second element 164. In some configurations, the channel 220 can extend below more than one wrap of the helically winding second element 164. In some configurations, a lip or a ridge 224 can be configured along or adjacent to the channel 220 and the lip or ridge 224 can be oriented to extend across the second element 164. The lip or ridge 224 can lift the second element 164 away from the outer surface of the main body 158 similar to the pad discussed above.

FIGS. 14A-14F illustrate another example embodiment of a patient-end connector 354. The patient-end connector 354 can comprise an integrally formed main body 358 and printed circuit board or PCB 368. In this embodiment, the second flattened region 172 of the tail 82 is cut off after the exposed wires 118 are soldered to the solder pads, and therefore no cover is used. The main body 358 can comprise a wire alignment component, such as a comb 382. The comb 382 can comprise alignment notches that receive the wires 166 to help keep the wires 166 separated from each other and taut during soldering to the PCB 368.

As shown, the PCB 368 extends through the diameter of the main body 358 and comprises a wider head part 368b and narrower stem part 368a. The head part 368b comprises solder pads 306. In the illustrated embodiment, the outer two solder pads 306a are positioned on the side of the head part 368b facing away from the comb 382, and the inner two solder pads 306b are positioned on the opposite side of the head part 368b, i.e., facing the comb 382. The outer two solder pads 306a can be configured to be soldered to the heater wires 14, and the inner two solder pads 306b can be configured to be soldered to the sensing wires 18. This arrangement advantageously increases the separation between the heater wire solder pads 306a and the sensing wire solder pads 306b to help reducing the likelihood of liquid bridging between them and potentially causing a short.

Figure 14A:
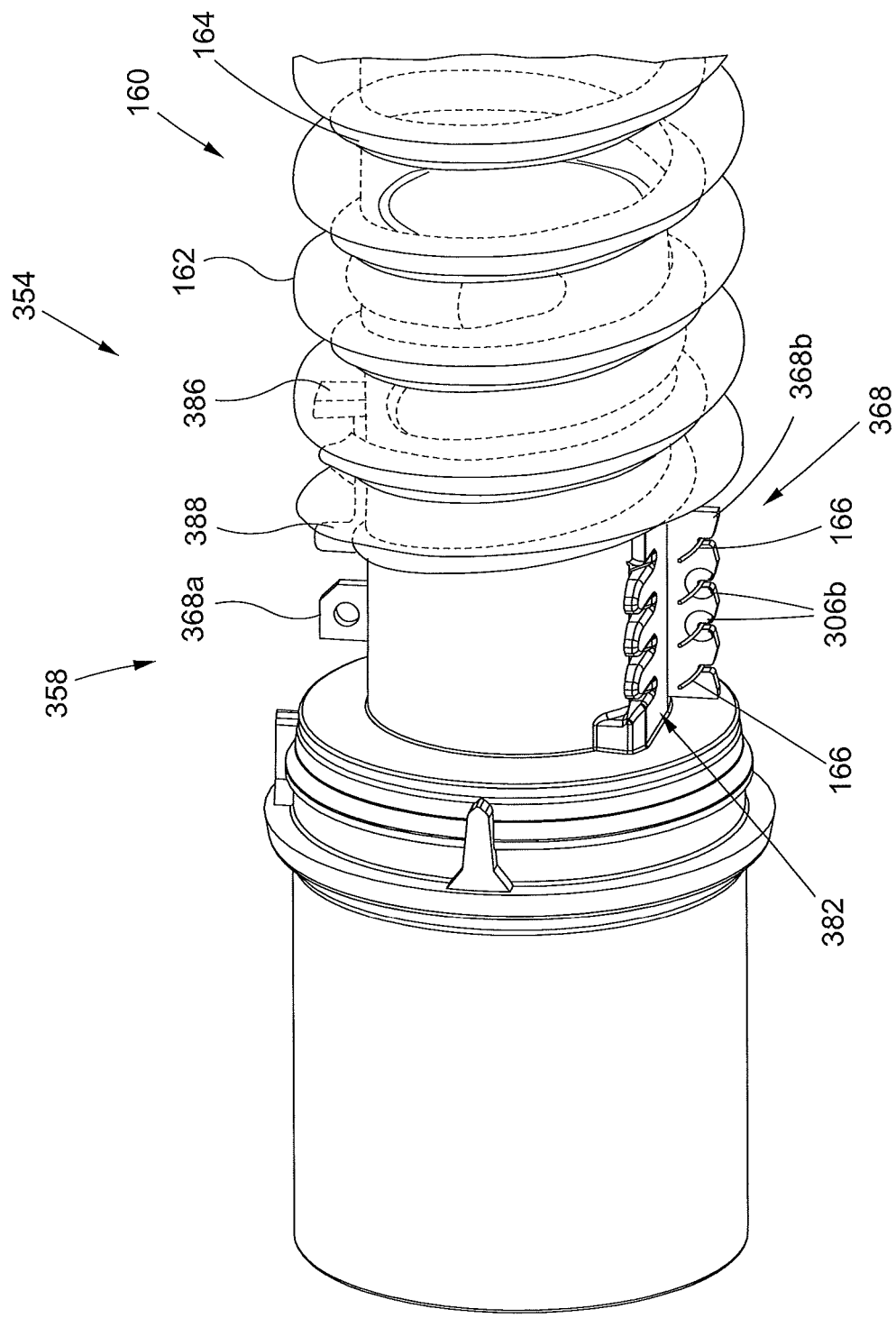
FIGS. 14A-14F are views of another example embodiment of a patient-end connector.

Similar to the chamber-end connector 352 described above, the patient-end connector 354 can comprise a first helical rib 494 that helps to hold the conduit 160 on the main body 358 during assembly by pressing into the first element 162, a guidance tab 386 that acts as a stop for the conduit 160 during assembly of the conduit 160 onto the main body 358, and a second helical rib 495 that acts as a liquid barrier to inhibit liquid from the conduit 160 from reaching the PCB 368. In the illustrated embodiment, the guidance tab 386 protrudes from the main body 358 normal to the main body 358. As shown in FIG. 14A, the first element 162 of the conduit 160 at the end of the conduit 160 threaded onto the connector 352 can be cut in the middle of the first element 162, and the main body 358 can be inserted into the conduit 160 until guidance tab 386 is positioned against the cut edge of the first element 162.

Figure 14B:
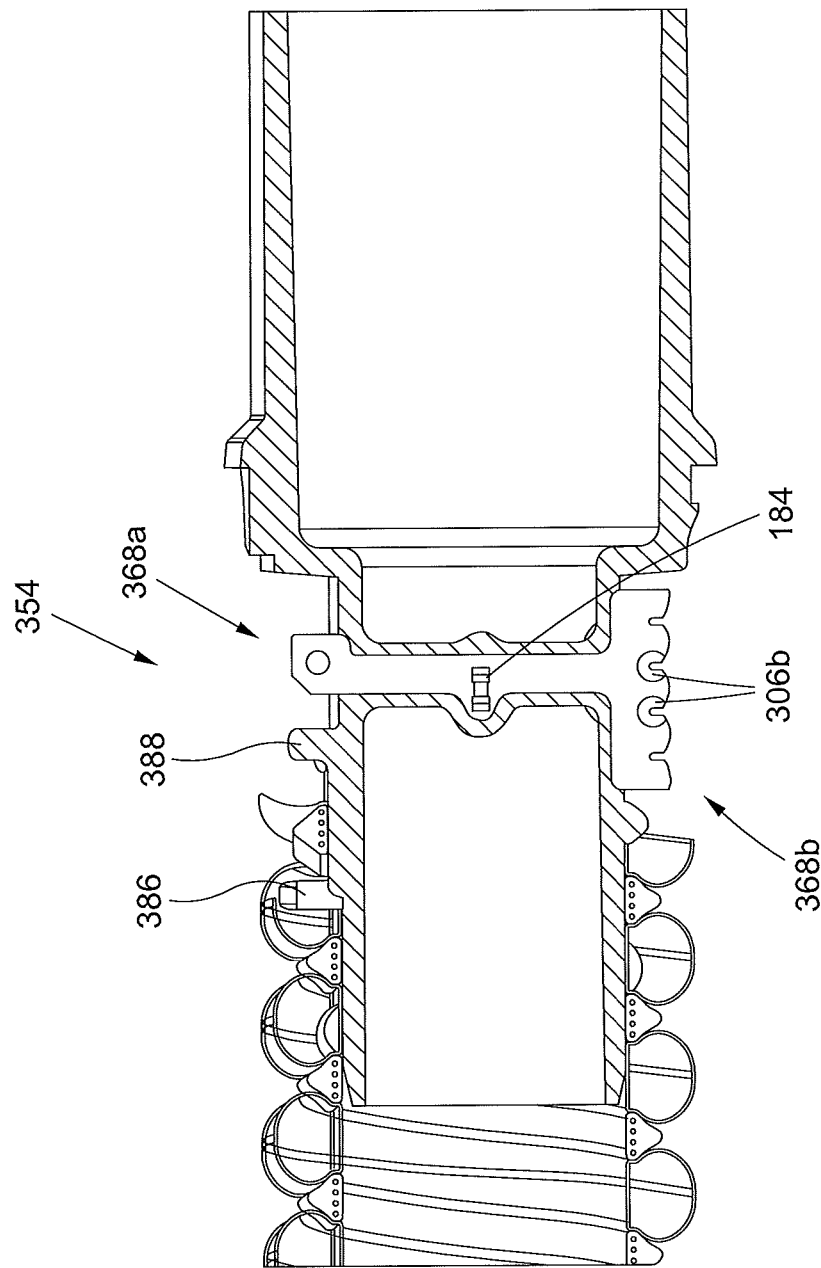
Figure 14C:
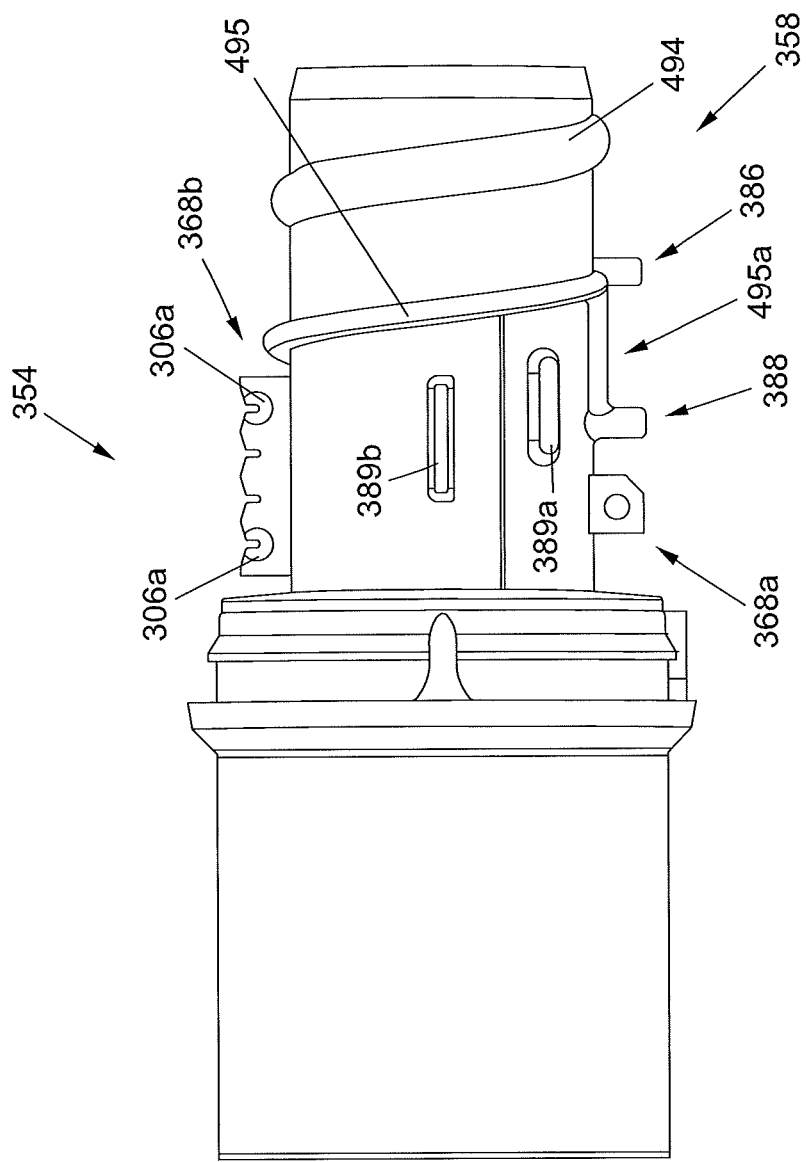

As shown in FIG. 14C, the second helical rib 495 comprises a longitudinal bridging segment 495a so that the second helical rib 495 completely encircles the main body 358 to create a liquid barrier. The guidance tab 396 is positioned at the end of the longitudinal bridging segment 495a closest to the first helical rib 494. A drift limit post 388 is positioned at the opposite end of the longitudinal bridging segment 495a from the guidance tab 396. The tail 82 extends over the longitudinal bridging segment 495a as it extends to the PCB 368. The drift limit post 388 helps inhibit the tail 82 from drifting too far toward the stem part 368a of the PCB 368 to help keep the tail 82 in the desired location during overmolding. As shown in FIG. 14B, the stem part 368a of the PCB 368 is offset or not centered relative to the head part 368b. This advantageously shifts the exposed end of the stem part 368a farther away from the drift limit post 388.

Figure 14D:
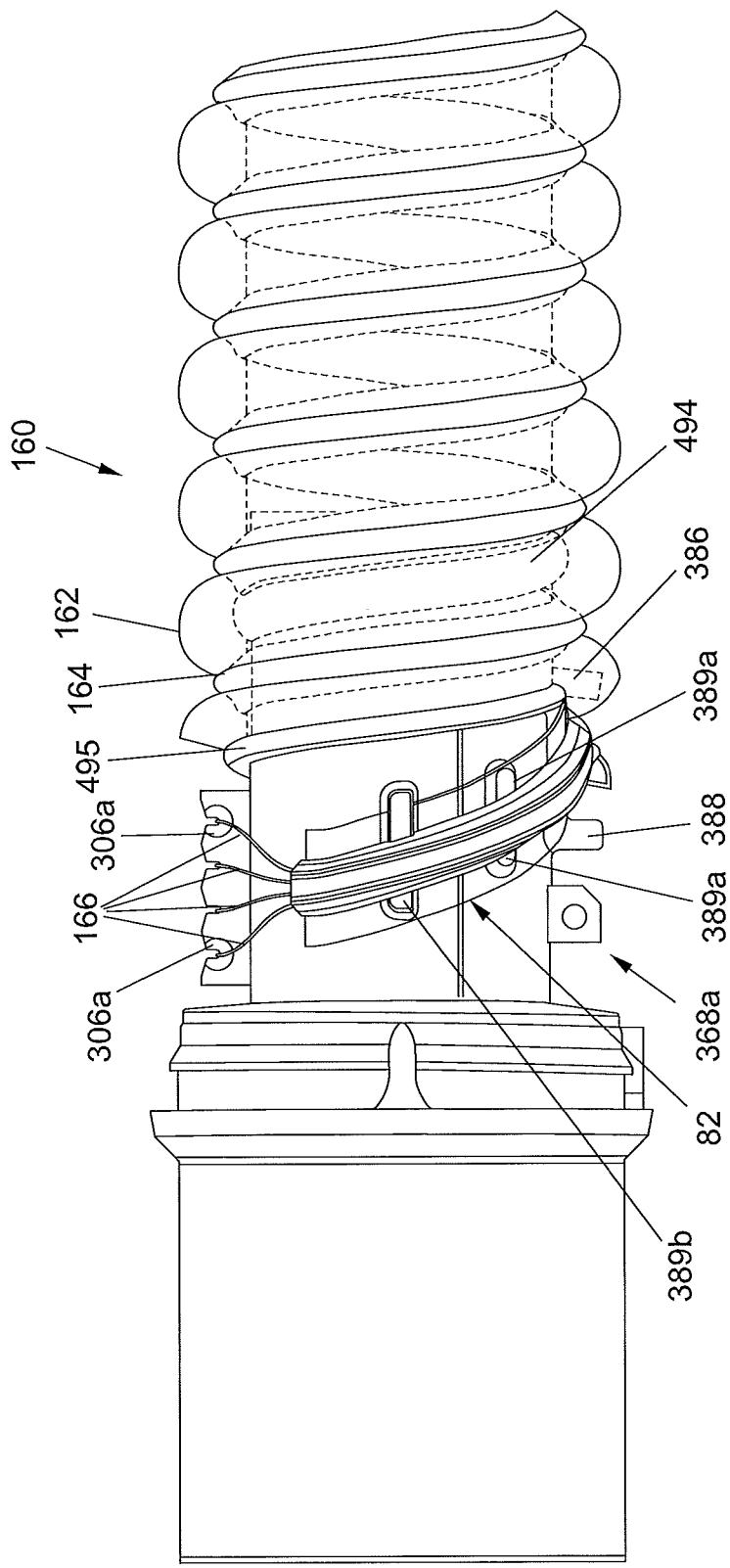
Figure 14E:
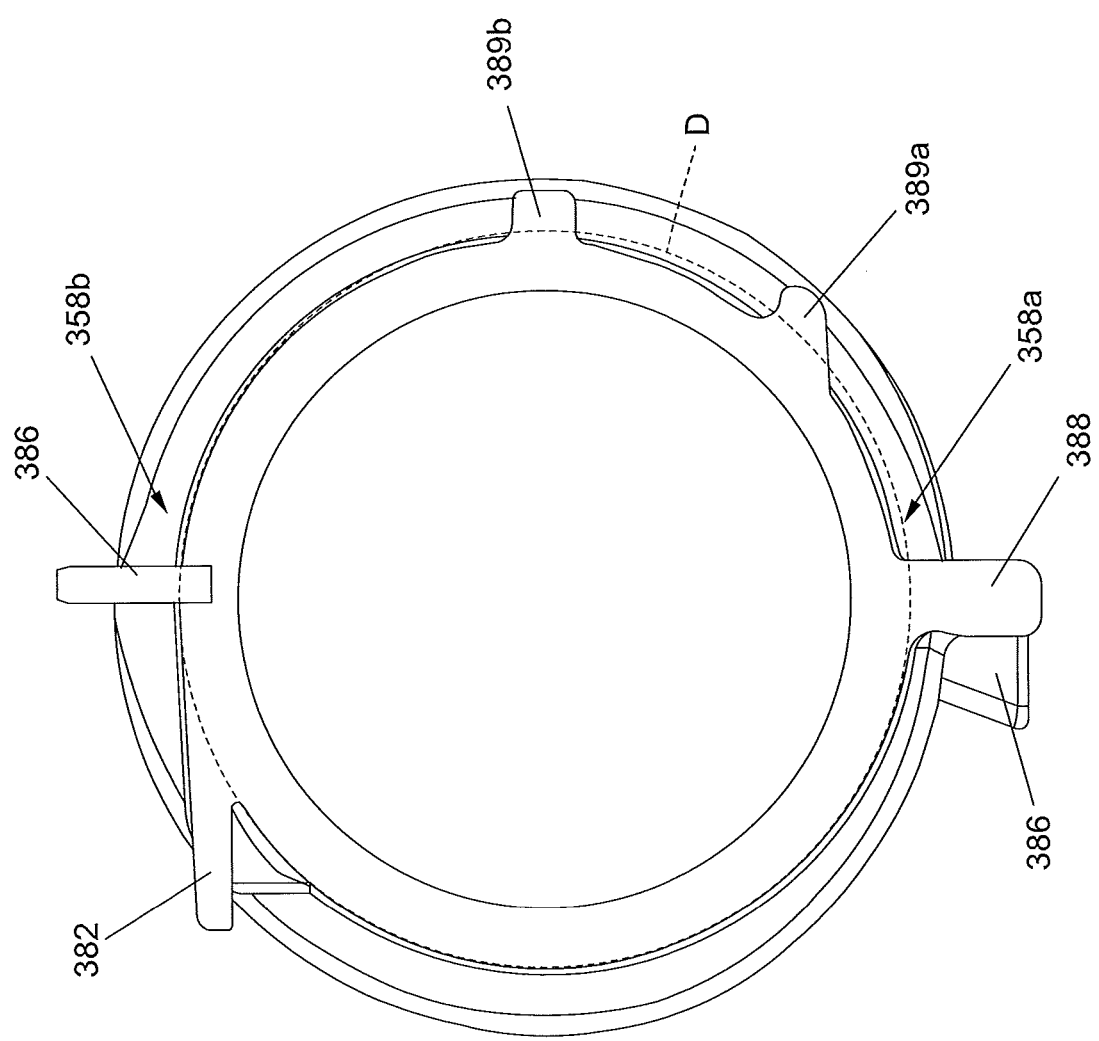
Figure 14F:
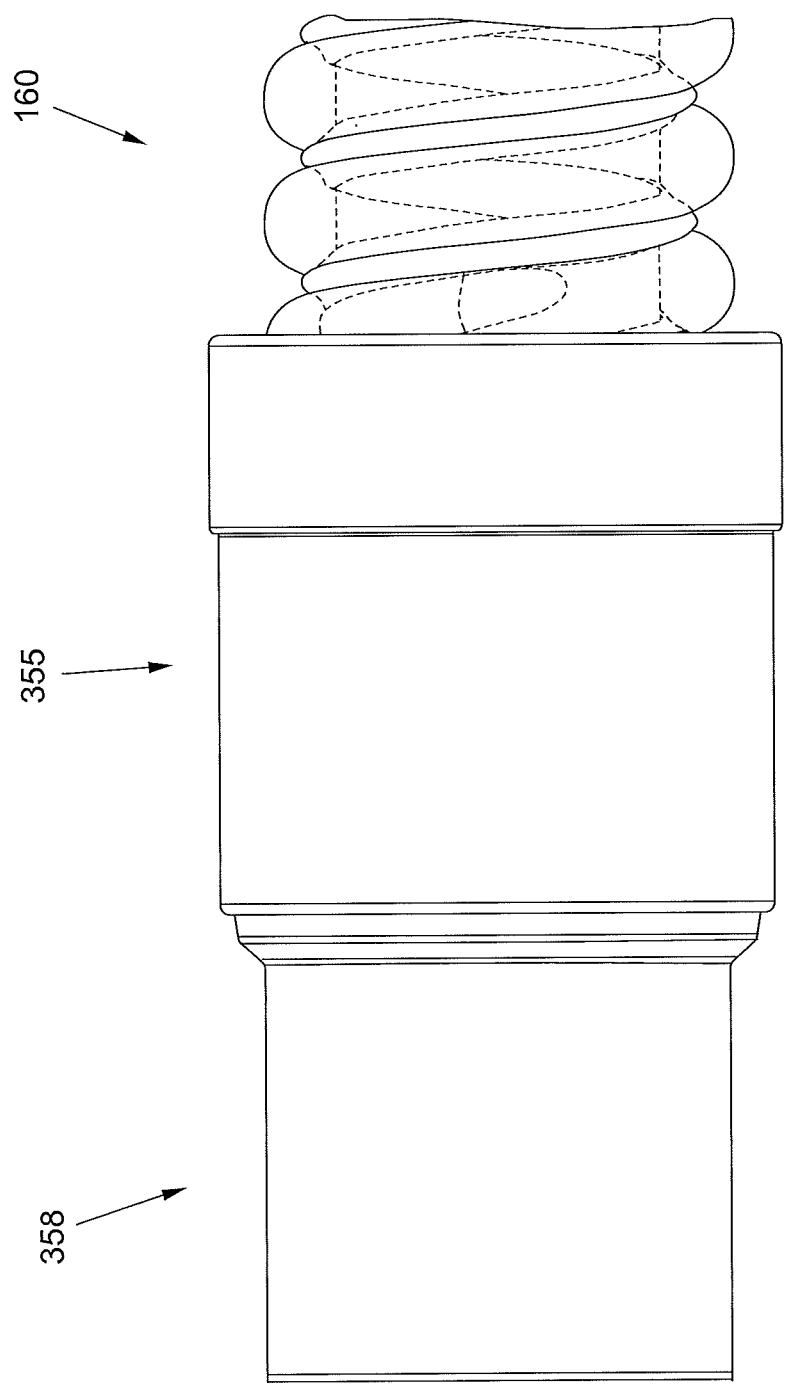

As described with respect to the chamber-end connectors 52, 352 and the embodiment of the patient-end connector 54 of FIGS. 12-13A, the connection between the conduit 160 and the main body 358 of the patient-end connector 354 and/or the connection between the conduit 160 and the PCB 368 can be overmolded. The patient-end connector 354 can comprise features to allow overmold material to flow into any gaps to better seal the interface between the conduit 160 and the main body 358. For example, as shown in FIGS. 14C and 14D, the main body 358 comprises a series of bridge members that lift the tail 82 away from the main body 358 to allow the overmold material to fully encapsulate the tail 82. The longitudinal bridging segment 495a of the second helical rib 495 forms the first bridge member. Two additional bridge members 389a, 389b are positioned between the longitudinal bridging segment 495a and the head part 368b of the PCB, although more or fewer bridge members are also possible. Additionally or alternatively, the main body 358 can have a reduced outer diameter in the region surrounding the bridge members. For example, as shown in FIG. 14E, the outer diameter can be reduced (compared to a diameter the main body 358 would have if circular, indicated by reference arc D in FIG. 14E) in the area 358a adjacent to the drift limit post 388 between the drift limit post 388 and bridge member 389a. In some configurations, the outer diameter can then gradually increase from region 358a to the region 358b adjacent the head part 368b of the PCB 368. This decreased outer diameter portion of the main body 358 can also help allow more overmold material to flow under the tail 82 to more completely encapsulate the tail 82. As shown in FIG. 14F, a cover member 355 can also connect to the main body 358 to enshroud the connection between the conduit 160 and the main body 358.

FIGS. 7B-7D illustrate an example embodiment of a midpoint assembly 400 that can be used to couple two conduit segments, such as the conduit segments 60 and 62 shown in FIG. 7. The midpoint assembly 400 as illustrated comprises a main body 402, a PCB 404, and a power diode 401. In some configurations, the midpoint assembly 400 may also comprise a sensor diode and a sensor, such as a thermistor. The midpoint assembly 400 can comprise various features similar in structure and/or function to those of the chamber-end connector 352 and the patient-end connector 354 shown and described herein, although the midpoint assembly 400 can comprise two each of many of these features, one at either end, as the midpoint assembly 400 is configured to couple to conduits at each end. For example, the midpoint assembly 400 comprises two alignment components, such as combs 410a, 410b. The first comb 410a extends generally perpendicularly to the PCB 404 on one side of the PCB 404, and the second comb 410b extends generally perpendicularly to the PCB 404 on the other side of the PCB 404. As shown in FIGS. 7B and 7D, solder pads 406 are alternated on either side of the PCB 404 to advantageously increase the separation between the adjacent solder pads 406 on each side of the PCB 404 to reduce the likelihood of shorts. Each end of the midpoint assembly 400 comprises a first helical rib 412 that allows for the conduit to be threaded onto the main body 402 and a second helical rib 414 that acts as a liquid barrier between the conduit and the PCB 404 and comprises a longitudinal bridging segment 414a so that the second helical rib 414 completely encircles the main body 402. Each end also comprises a guidance tab 416 at one end of the longitudinal bridging segment 414a. Each end further comprises two bridging members 420 that lift tails of the conduit segments away from the main body 402 to allow overmold material to fully encapsulate the tails.

Figure 7E:
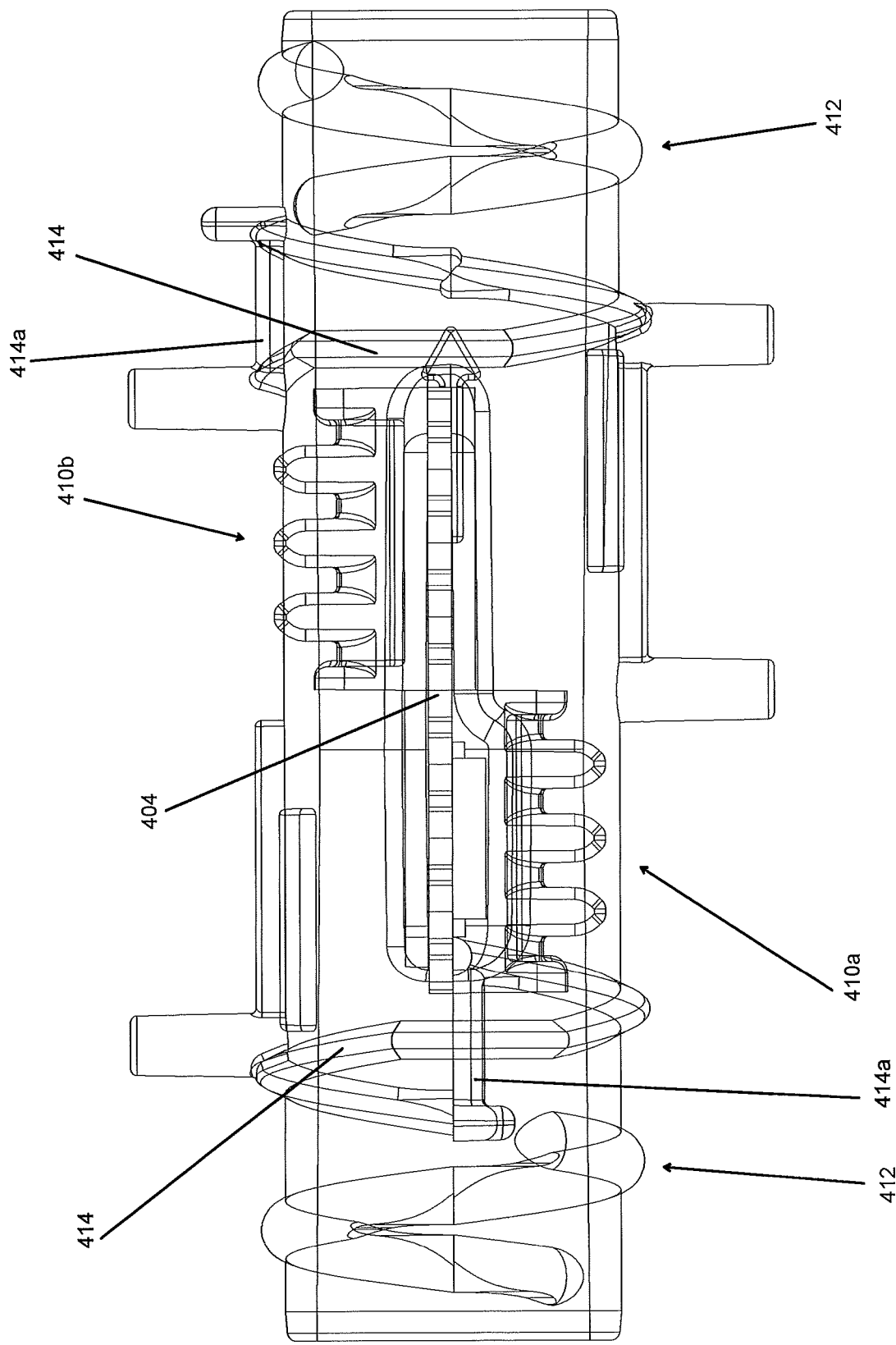
FIGS. 7E and 7F illustrates another example embodiment of a midpoint assembly that can be used to joint conduit segments.
Figure 7F:
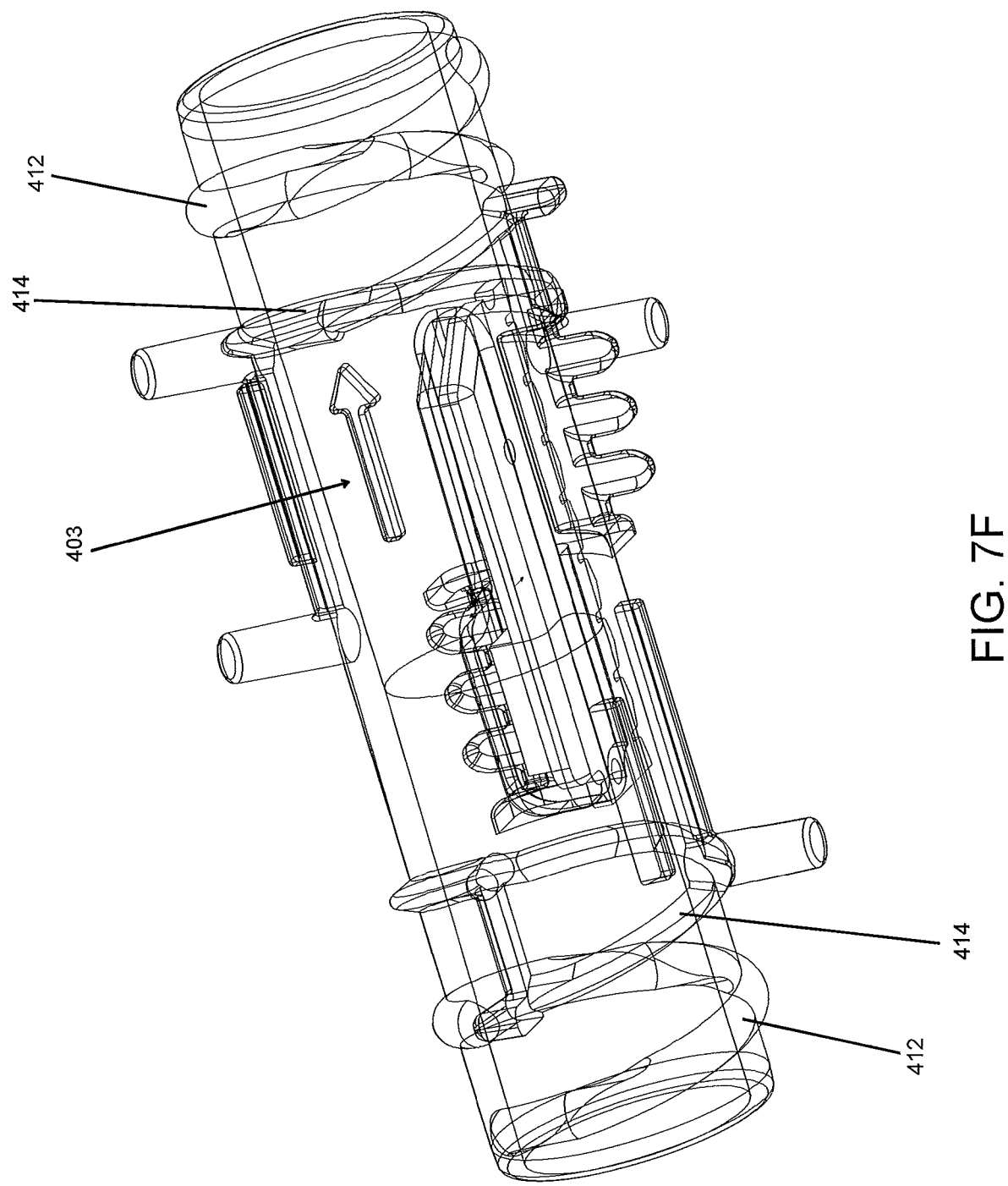

FIGS. 7E-7F illustrate another example embodiment of a midpoint assembly. The illustrated midpoint assembly can be similar to the midpoint assembly 400 of FIGS. 7B-7D. However, in the embodiment of FIGS. 7B-7D, the first helical rib 412 and second helical rib 414 on the chamber end of the midpoint assembly and the first helical rib 412 and second helical rib 414 on the patient end of the midpoint assembly begin and end at substantially (e.g., within 5° or 10°) the same circumferential location. The longitudinal bridging segments 414a on the chamber and patient ends of the midpoint assembly can be positioned at substantially (e.g., within 5° or 10°) the same circumferential location. In the embodiment of FIGS. 7E-7F, the start and end of the first 412 and second 414 helical ribs on one of the chamber end and patient end of the midpoint assembly are offset or displaced in a circumferential direction relative to the start and end of the first 412 and second 414 helical ribs on the other of the chamber end and patient end of the midpoint assembly. In some embodiments, the longitudinal bridging segment 414a on one of the chamber and patient ends of the midpoint assembly is offset or displaced in a circumferential direction relative to the longitudinal bridging segment 414*a* on the other of the chamber and patient ends of the midpoint assembly. As shown in the illustrated configuration, the start and end of the first and second helical ribs and/or the longitudinal bridging segment on one of the chamber and patient ends of the midpoint assembly is offset or displaced by 90° in a circumferential direction relative to the start and end of the first and second helical ribs and/or the longitudinal bridging segment on the other of the chamber and patient ends. This arrangement advantageously allows the chamber end connector, midpoint assembly, and patient end connector to be placed in an assembly jig in the correct orientation during manufacturing without kinking one of the tube segments. In some configurations, the midpoint assembly can include an indicator to show an orientation of the midpoint assembly. For example, in the illustrated configuration, the midpoint assembly includes an arrow 403 pointing toward the patient end of the midpoint assembly.

In some configurations, the wires exposed in one or more of the tails 20, 30, 70, 72, 80, 82 can be tinned prior to being soldered. In some configurations, the wires exposed in one or more of the tails 20, 30, 70, 72, 80, 82 can be tinned and the respective second flattened portion 36 or second flattened region 122, 172 is omitted. In some configurations, the wires exposed in one or more of the tails 20, 30, 70, 72, 80, 82 can be tinned and the respective second flattened portion 36 or second flattened region 122, 172 is not omitted. The tinning of wires can improve and simplify the soldering process. In addition, the tinning of wires can reduce the likelihood of wires crossing or making contact with each other. In some configurations, the wires exposed in one or more of the tails 20, 30, 70, 72, 80, 82 can be tinned and the respective cover 124, 174 still is used to secure portions of the one or more of the tails 20, 30, 70, 72, 80, 82 in position. In some configurations, the wires exposed in one or more of the tails 20, 30, 70, 72, 80, 82 can be tinned and the respective cover 124, 174 is not used to secure portions of the one or more of the tails 20, 30, 70, 72, 80, 82 in position. In some configurations, the wires exposed in one or more of the tails 20, 30, 70, 72, 80, 82 can be not tinned and the respective cover 124, 174 is used to secure portions of the one or more of the tails 20, 30, 70, 72, 80, 82 in position, as described above. In some configurations, the wires exposed in one or more of the tails 20, 30, 70, 72, 80, 82 can be not tinned and the respective cover 124, 174 is not used to secure portions of the one or more of the tails 20, 30, 70, 72, 80, 82 in position. Any other suitable configuration can be used.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numerical values provided are provided as examples and are not limited to those specific values; rather, the scope of the disclosure includes values that are about, approximately, or within a reasonable range of the provided values as reasonable under the circumstances. In other words, in order to avoid mathematical rigidity of magnitude terms (e.g., a number), where specific numbers are identified as a value, it is expressly contemplated that the value includes inconsequential variations that do not frustrate the function or purpose achieved by the magnitude term; phrases such as "about," "approximately," and the like should be implied in association with such magnitude terms and the doctrine of equivalents is being relied upon to deal with inconsequential variations of these magnitude terms. Similarly, phrases preceded by a term such as "substantially" or "generally" include the recited phrase and should be interpreted based on the circumstances (e.g., as much as reasonably possible under the circumstances). For example, "generally perpendicularly" includes "perpendicularly."

What is claimed is:

1. A medical tube configured to deliver respiratory gases to a patient comprising:
    a first elongate member and a second elongate member, the second elongate member comprising a material providing reinforcing properties and having a plurality of wires embedded therein;
    wherein the second elongate member terminates in a tail, the tail comprising a flattened portion that precedes an exposed portion, the exposed portion of the tail exposing at least a portion of the plurality of wires, wherein the material in the second elongate member ends prior to the exposed portion;
    wherein the flattened portion has a width and a height, the width of the flattened portion being greater than a width of the second elongate member apart from the tail, and the height of the flattened portion being less than a height of the second elongate member apart from the tail; and
    wherein within the flattened portion:
        the plurality of wires are embedded within the material; and
        the plurality of wires are spaced further apart from each other than in the second elongate member apart from the tail.

2. The medical tube as claimed in claim 1, wherein the second elongate member is helically wound.

3. The medical tube as claimed in claim 1, wherein the second elongate member comprises a bead.

4. The medical tube as claimed in claim 1, wherein the medical tube comprises a lumen and the second elongate member forms a portion of a wall surrounding the lumen and is configured to be in contact with the gases flow.

5. The medical tube as claimed in claim 4, wherein the first elongate member comprises a hollow body, is helically wound between adjacent turns of the second elongate member, and forms a portion of the wall surrounding the lumen and is configured to be in contact with the gases flow.

6. The medical tube as claimed in claim 1, wherein the second elongate member comprises an unflattened portion that is separated from the first elongate member and positioned between an end of the first elongate member and the flattened portion of the tail.

7. The medical tube as claimed in claim 1, wherein the plurality of wires comprises at least one heater wire or at least one sensing wire.

8. The medical tube as claimed in claim 7, wherein the at least one sensing wire is used to sense one of temperature, flow, humidity, or pressure.

9. The medical tube as claimed in claim 1, wherein the plurality of wires comprises four wires.

10. The medical tube as claimed in claim 1, wherein the plurality of wires comprises two heater wires and two sensing wires.

11. The medical tube as claimed in claim 1, wherein the tail comprises a second flattened portion following the exposed portion.

12. The medical tube as claimed in claim 1, wherein the plurality of wires are relatively more separated in the exposed portion than in an unflattened portion of the second elongate member.

13. The medical tube as claimed in claim 1, wherein the spacing between adjacent wires of the plurality of wires is configured for attachment to a printed circuit board.

14. The medical tube as claimed in claim 1, wherein the spacing between adjacent wires of the plurality of wires in the flattened portion is at least 1.0 mm.

15. The medical tube as claimed in claim 1, further comprising a connector joined to an end of the medical tube.

16. The medical tube as claimed in claim 15, wherein the connector comprises at least one of a patient-end connector or a chamber-end connector.

17. The medical tube as claimed in claim 15, wherein the connector is configured to form an electrical and pneumatic connection between the medical tube and a respiratory system component.

18. The medical tube as claimed in claim 15, wherein the tail is connected to the connector.

19. The medical tube as claimed in claim 15, wherein the connector comprises a printed circuit board and the tail is connected to the printed circuit board.

20. The medical tube as claimed in claim 19, wherein the printed circuit board is integrated into a housing of the connector using overmolding.

21. The medical tube as claimed in claim 20, wherein the printed circuit board spans a diameter of a passage through the housing.

* * * * *